US008864652B2

(12) United States Patent
Diolaiti et al.

(10) Patent No.: US 8,864,652 B2
(45) Date of Patent: Oct. 21, 2014

(54) MEDICAL ROBOTIC SYSTEM PROVIDING COMPUTER GENERATED AUXILIARY VIEWS OF A CAMERA INSTRUMENT FOR CONTROLLING THE POSITIONING AND ORIENTING OF ITS TIP

(75) Inventors: Nicola Diolaiti, Palo Alto, CA (US); David Q. Larkin, Menlo Park, CA (US); Daniel Gomez, Mountain View, CA (US); Tabish Mustafa, Mountain View, CA (US); Paul W. Mohr, Mountain View, CA (US); Paul Lilagan, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1267 days.

(21) Appl. No.: 12/336,713

(22) Filed: Dec. 17, 2008

(65) Prior Publication Data
US 2009/0326556 A1   Dec. 31, 2009

Related U.S. Application Data

(63) Continuation-in-part of application No. 12/163,087, filed on Jun. 27, 2008.

(60) Provisional application No. 61/101,384, filed on Sep. 30, 2008.

(51) Int. Cl.
*A61B 1/00* (2006.01)
*A61B 1/04* (2006.01)
(Continued)

(52) U.S. Cl.
CPC ..... *A61B 19/5244* (2013.01); *A61B 2019/2296* (2013.01); *A61B 5/065* (2013.01);
(Continued)

(58) Field of Classification Search
CPC .. A61B 1/0053; A61B 1/008; A61B 1/00149; A61B 2019/501; A61B 2019/502; A61B 2019/508; A61B 2019/2211; A61B 2019/2223; A61B 2019/2276; A61B 19/2203; A61B 19/5244; A61B 19/22; A61B 5/065; A61B 5/066; A61B 5/067; A61B 5/068
USPC ......... 600/103, 104, 117, 145, 173, 106, 109, 600/160
See application file for complete search history.

(56) References Cited

U.S. PATENT DOCUMENTS 4,644,237 A   2/1987  Frushour et al.
4,791,934 A   12/1988 Brunnett
(Continued)

FOREIGN PATENT DOCUMENTS

EP   812662 A1    12/1997
EP   1125557 A2   8/2001
(Continued)

OTHER PUBLICATIONS

Vertut, Jean et al., Robot Technology: Teleoperation and Robotics Evolution and Development, 1986, vol. 3A, 332 pages, English translation Prentice-Hall, Inc., Inglewood Cliffs, NJ, USA.
(Continued)

*Primary Examiner* — Anhtuan T Nguyen
*Assistant Examiner* — William Chou

(57) ABSTRACT

A medical robotic system includes an entry guide with surgical tools and a camera extending out of its distal end. To supplement the view provided by an image captured by the camera, an auxiliary view including articulatable arms of the surgical tools and/or camera is generated from sensed or otherwise determined information about their positions and orientations and displayed on a display screen from the perspective of a specified viewing point. Intuitive control is provided to an operator with respect to the auxiliary view while the operator controls the positioning and orienting of the camera.

16 Claims, 17 Drawing Sheets

(51) Int. Cl.
*A61B 1/06* (2006.01)
*A61B 5/06* (2006.01)
*G09B 23/28* (2006.01)
*G06T 7/00* (2006.01)
*A61B 1/05* (2006.01)
*A61B 1/313* (2006.01)
*A61B 19/00* (2006.01)
*A61B 17/00* (2006.01)

(52) U.S. Cl.
CPC ......... *A61B 2019/5289* (2013.01); *A61B 19/52* (2013.01); *G09B 23/285* (2013.01); *A61B 1/00149* (2013.01); *A61B 2019/2234* (2013.01); *A61B 2019/502* (2013.01); *G06T 7/004* (2013.01); *A61B 19/5212* (2013.01); *A61B 2019/2269* (2013.01); *A61B 1/0005* (2013.01); *A61B 1/00009* (2013.01); *A61B 1/05* (2013.01); *A61B 19/30* (2013.01); *A61B 1/00039* (2013.01); *A61B 1/313* (2013.01); *A61B 19/2203* (2013.01); *A61B 2019/5274* (2013.01); *A61B 2019/5291* (2013.01); *A61B 2019/2223* (2013.01); *A61B 2017/00119* (2013.01)
USPC ............ 600/102; 600/117; 600/173; 600/109

(56) References Cited

U.S. PATENT DOCUMENTS

| | | |
|---|---|---|
| 4,831,549 A | 5/1989 | Red et al. |
| 4,837,703 A | 6/1989 | Kakazu et al. |
| 4,979,949 A | 12/1990 | Matsen, III et al. |
| 5,086,401 A | 2/1992 | Glassman et al. |
| 5,230,338 A | 7/1993 | Allen et al. |
| 5,343,385 A | 8/1994 | Joskowicz et al. |
| 5,408,409 A | 4/1995 | Glassman et al. |
| 5,417,210 A | 5/1995 | Funda et al. |
| 5,528,955 A | 6/1996 | Hannaford et al. |
| 5,704,897 A * | 1/1998 | Truppe ................. 600/117 |
| 5,748,767 A * | 5/1998 | Raab ................. 382/128 |
| 5,749,362 A | 5/1998 | Funda et al. |
| 5,755,725 A | 5/1998 | Druais |
| 5,820,545 A | 10/1998 | Arbter et al. |
| 5,820,623 A | 10/1998 | Ng |
| 5,831,408 A | 11/1998 | Jacobus et al. |
| 5,835,693 A | 11/1998 | Lynch et al. |
| 5,876,325 A * | 3/1999 | Mizuno et al. ............. 600/102 |
| 5,950,629 A | 9/1999 | Taylor et al. |
| 5,987,591 A | 11/1999 | Jyumonji |
| 6,115,053 A | 9/2000 | Perlin |
| 6,120,433 A | 9/2000 | Mizuno et al. |
| 6,184,868 B1 | 2/2001 | Shahoian et al. |
| 6,204,620 B1 | 3/2001 | McGee et al. |
| 6,224,542 B1 | 5/2001 | Chang et al. |
| 6,325,808 B1 | 12/2001 | Bernard et al. |
| 6,342,889 B1 | 1/2002 | Callahan |
| 6,371,909 B1 * | 4/2002 | Hoeg et al. ............. 600/173 |
| 6,398,726 B1 | 6/2002 | Ramans et al. |
| 6,424,885 B1 | 7/2002 | Niemeyer et al. |
| 6,442,417 B1 | 8/2002 | Shahidi et al. |
| 6,456,901 B1 | 9/2002 | Xi et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,522,906 B1 | 2/2003 | Salisbury, Jr. et al. |
| 6,574,355 B2 * | 6/2003 | Green ................. 382/128 |
| 6,643,563 B2 | 11/2003 | Hosek et al. |
| 6,645,196 B1 | 11/2003 | Nixon et al. |
| 6,648,816 B2 * | 11/2003 | Irion et al. ............. 600/173 |
| 6,659,939 B2 | 12/2003 | Moll et al. |
| 6,770,081 B1 | 8/2004 | Cooper et al. |
| 6,837,883 B2 | 1/2005 | Moll et al. |
| 6,847,922 B1 | 1/2005 | Wampler, II |
| 6,926,709 B2 | 8/2005 | Bieger et al. |
| 6,991,627 B2 | 1/2006 | Madhani et al. |
| 7,041,053 B2 | 5/2006 | Miyake |
| 7,155,315 B2 | 12/2006 | Niemeyer et al. |
| 7,181,315 B2 | 2/2007 | Watanabe et al. |
| 7,194,118 B1 | 3/2007 | Harris et al. |
| 7,491,198 B2 | 2/2009 | Kockro |
| 7,725,214 B2 | 5/2010 | Diolaiti |
| 7,806,891 B2 | 10/2010 | Nowlin et al. |
| 7,819,859 B2 | 10/2010 | Prisco et al. |
| 7,963,913 B2 | 6/2011 | Devengenzo et al. |
| 7,979,157 B2 | 7/2011 | Anvari |
| 7,996,110 B2 | 8/2011 | Lipow et al. |
| 8,062,288 B2 | 11/2011 | Cooper et al. |
| 8,120,301 B2 | 2/2012 | Goldberg et al. |
| 8,130,907 B2 | 3/2012 | Maurer, Jr. et al. |
| 8,155,479 B2 | 4/2012 | Hoffman et al. |
| 8,170,716 B2 | 5/2012 | Coste-Maniere et al. |
| 8,256,319 B2 | 9/2012 | Cooper et al. |
| 8,315,720 B2 | 11/2012 | Mohr et al. |
| 8,335,590 B2 | 12/2012 | Costa et al. |
| 8,620,473 B2 | 12/2013 | Diolaiti et al. |
| 2001/0035871 A1 | 11/2001 | Bieger et al. |
| 2002/0045905 A1 | 4/2002 | Gerbi et al. |
| 2002/0120188 A1 | 8/2002 | Brock et al. |
| 2003/0032878 A1 | 2/2003 | Shahidi |
| 2003/0055410 A1 | 3/2003 | Evans et al. |
| 2003/0109780 A1 | 6/2003 | Coste-Maniere et al. |
| 2003/0114730 A1 * | 6/2003 | Hale et al. ............. 600/114 |
| 2003/0167103 A1 | 9/2003 | Tang et al. |
| 2003/0225479 A1 | 12/2003 | Waled |
| 2004/0077940 A1 | 4/2004 | Kienzle et al. |
| 2004/0106916 A1 | 6/2004 | Quaid et al. |
| 2004/0238732 A1 | 12/2004 | State et al. |
| 2004/0249508 A1 | 12/2004 | Suita et al. |
| 2004/0254679 A1 | 12/2004 | Nagasaka |
| 2005/0022158 A1 | 1/2005 | Launay et al. |
| 2005/0054895 A1 * | 3/2005 | Hoeg et al. ............. 600/117 |
| 2005/0059960 A1 | 3/2005 | Simaan et al. |
| 2005/0096502 A1 * | 5/2005 | Khalili ................. 600/106 |
| 2005/0113640 A1 * | 5/2005 | Saadat et al. ............. 600/106 |
| 2005/0203380 A1 | 9/2005 | Sauer et al. |
| 2005/0228365 A1 | 10/2005 | Wang et al. |
| 2005/0251113 A1 | 11/2005 | Kienzle, III |
| 2006/0142657 A1 | 6/2006 | Quaid et al. |
| 2006/0258938 A1 | 11/2006 | Hoffman et al. |
| 2006/0261770 A1 | 11/2006 | Kishi et al. |
| 2007/0013336 A1 | 1/2007 | Nowlin et al. |
| 2007/0032906 A1 * | 2/2007 | Sutherland et al. ............. 700/248 |
| 2007/0038080 A1 | 2/2007 | Salisbury et al. |
| 2007/0135803 A1 | 6/2007 | Belson |
| 2007/0142968 A1 | 6/2007 | Prisco et al. |
| 2007/0255454 A1 | 11/2007 | Dariush |
| 2007/0265491 A1 | 11/2007 | Krag et al. |
| 2007/0270650 A1 | 11/2007 | Eno et al. |
| 2007/0283970 A1 | 12/2007 | Mohr et al. |
| 2007/0287884 A1 | 12/2007 | Schena |
| 2007/0287992 A1 | 12/2007 | Diolaiti et al. |
| 2008/0004603 A1 | 1/2008 | Larkin et al. |
| 2008/0033240 A1 | 2/2008 | Hoffman et al. |
| 2008/0065105 A1 | 3/2008 | Larkin et al. |
| 2008/0065109 A1 | 3/2008 | Larkin |
| 2008/0071291 A1 | 3/2008 | Duval et al. |
| 2008/0081992 A1 | 4/2008 | Kagermeier |
| 2008/0118115 A1 | 5/2008 | Williamson |
| 2008/0140087 A1 | 6/2008 | Barbagli |
| 2008/0161830 A1 | 7/2008 | Sutherland et al. |
| 2008/0188986 A1 | 8/2008 | Hoppe |
| 2008/0243142 A1 | 10/2008 | Gildenberg |
| 2008/0247506 A1 | 10/2008 | Maschke |
| 2008/0287963 A1 | 11/2008 | Rogers et al. |
| 2009/0012531 A1 | 1/2009 | Quaid et al. |
| 2009/0024142 A1 | 1/2009 | Ruiz Morales |
| 2009/0036902 A1 | 2/2009 | DiMaio et al. |
| 2009/0088634 A1 | 4/2009 | Zhao et al. |
| 2009/0192524 A1 | 7/2009 | Itkowitz et al. |
| 2009/0228145 A1 | 9/2009 | Hodgson et al. |
| 2009/0248036 A1 | 10/2009 | Hoffman et al. |
| 2009/0259105 A1 * | 10/2009 | Miyano et al. ............. 600/127 |
| 2009/0326318 A1 | 12/2009 | Tognaccini et al. |

(56) References Cited

U.S. PATENT DOCUMENTS

| | | |
|---|---|---|
| 2009/0326552 A1 | 12/2009 | Diolaiti |
| 2009/0326553 A1 | 12/2009 | Mustufa et al. |
| 2009/0326711 A1 | 12/2009 | Chang et al. |
| 2010/0004505 A1* | 1/2010 | Umemoto et al. ............ 600/106 |
| 2010/0036198 A1* | 2/2010 | Tacchino et al. ............. 600/106 |
| 2010/0106356 A1 | 4/2010 | Trepagnier et al. |
| 2010/0198232 A1 | 8/2010 | Diolaiti |
| 2010/0249657 A1 | 9/2010 | Nycz et al. |
| 2011/0040305 A1 | 2/2011 | Gomez et al. |
| 2011/0040404 A1 | 2/2011 | Diolaiti et al. |
| 2011/0071675 A1 | 3/2011 | Wells et al. |
| 2011/0196199 A1 | 8/2011 | Donhowe et al. |
| 2011/0202068 A1 | 8/2011 | Diolaiti et al. |
| 2012/0059391 A1 | 3/2012 | Diolaiti et al. |
| 2012/0059392 A1 | 3/2012 | Diolaiti |
| 2013/0231680 A1 | 9/2013 | Diolaiti et al. |
| 2014/0055489 A1 | 2/2014 | Itkowitz et al. |

FOREIGN PATENT DOCUMENTS

| | | |
|---|---|---|
| JP | H08154321 A | 6/1996 |
| JP | H11000309 A | 6/1999 |
| JP | 2007029232 A | 2/2007 |
| JP | 2009006410 A | 1/2009 |
| JP | 2009012106 A | 1/2009 |
| WO | WO-2004014244 | 2/2004 |
| WO | WO-2006079108 A1 | 7/2006 |
| WO | WO-2007030173 A1 | 3/2007 |
| WO | WO-2007047782 A2 | 4/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO2008/103383 A1 | 8/2008 |
| WO | WO-2009034477 | 3/2009 |
| WO | WO-2009037576 A2 | 3/2009 |
| WO | WO-2009158164 A1 | 12/2009 |
| WO | WO-2010039394 A1 | 4/2010 |

OTHER PUBLICATIONS

PCT/US09/56078 International Search Report and Written Opinion of the International Searching Authority, mailed Jan. 20, 2010, 12 pages.

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.

Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.

International Search Report and Written Opinion for Application No. PCT/US2012/064379, mailed on Mar. 29, 2013, 12 pages.

International Search Report and Written Opinion for Application No. PCT/US2012/064400, mailed on Mar. 27, 2013, 10 pages.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

PCT/US07/71850 International Search Report and Written Opinion of the International Searching Authority, mailed Feb. 13, 2009, 9 pages.

PCT/US09/46234 International Search Report and Written Opinion of the International Searching Authority, mailed Sep. 9, 2009, 13 pages.

PCT/US10/28886 International Search Report and Written Opinion of the International Searching Authority, mailed Jul. 6, 2010, 11 pages.

PCT/US10/28897 International Search Report and Written Opinion of the International Searching Authority, mailed Jul. 19, 2010, 16 pages.

PCT/US10/38246 International Search Report and Written Opinion of the International Searching Authority, mailed Sep. 14, 2010, 17 pages.

PCT/US2011/036109 International Search Report and Written Opinion of the International Searching Authority, mailed Oct. 19, 2011, 16 pages.

PCT/US2011/036109 Invitation to Pay Additional Fees and Partial International Search Report, mailed Aug. 18, 2011, 5 pages.

Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

* cited by examiner

MEDICAL ROBOTIC SYSTEM PROVIDING COMPUTER GENERATED AUXILIARY VIEWS OF A CAMERA INSTRUMENT FOR CONTROLLING THE POSITIONING AND ORIENTING OF ITS TIP

CROSS REFERENCE TO RELATED APPLICATIONS

This patent application claims benefit of the U.S. Provisional Patent Application No. 61/101,384, filed Sep. 30, 2008 by inventors Nicola Diolaiti et al., entitled MEDICAL ROBOTIC SYSTEM PROVIDING COMPUTER GENERATED AUXILIARY VIEWS OF A CAMERA INSTRUMENT FOR CONTROLLING THE POSITIONING AND ORIENTING OF ITS TIP, and is a continuation-in-part to U.S. application Ser. No. 12/163,087 filed Jun. 27, 2008, which are incorporated herein by reference.

FIELD OF THE INVENTION

The present invention generally relates to medical robotic systems and in particular, to a medical robotic system providing computer generated auxiliary views of a camera instrument for controlling the positioning and orienting of its tip.

BACKGROUND OF THE INVENTION

Medical robotic systems such as systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulatable camera and a plurality of articulatable surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

Since the entry guide generally has a relatively small diameter in order to fit through a minimally invasive incision or a natural body orifice, a number of problems may arise while teleoperating the surgical tools to perform the medical procedure and the camera to view it. For example, because the camera instrument is bundled with the surgical tools, it is limited in its positioning relative to the surgical tools and consequently, its view of the surgical tools.

Thus, although the tips of the articulatable surgical tools may be kept in the field of view of the camera, links coupled by controllable joints which facilitate the articulatability of the surgical tools may not be in the field of view of the camera. As a consequence, the links of the surgical tools may inadvertently collide with each other (or with a link of the camera instrument) during the performance of a medical procedure and as a result, cause harm to the patient or otherwise adversely impact the performance of the medical procedure.

Also, since the articulatable camera instrument is generally incapable of viewing its own controllable linkage, operator movement of the camera tip is especially a concern where collisions with the surgical tool links are to be avoided. Further, when intuitive control is provided to assist the operator in teleoperatively moving the surgical tools and camera, the motions of the linkages required to produce such intuitive motions of the tips of the tools and camera may not be obvious or intuitive to the operator, thus making it even more difficult for the operator to avoid collisions between links that are outside the field of view of the camera.

OBJECTS AND SUMMARY OF THE INVENTION

Accordingly, one object of one or more aspects of the present invention is a method implemented in a medical robotic system that provides a computer generated auxiliary view of a camera for positioning and orienting the camera.

Another object of one or more aspects of the present invention is a method implemented in a medical robotic system that provides intuitive control to an operator controlling the positioning and orienting of a camera while viewing an auxiliary view of the camera.

Another object of one or more aspects of the present invention is a method implemented in a medical robotic system that improves an operator's understanding of the configuration of linkages of articulatable instruments that are outside of the field of view of a camera while controllably positioning and orienting the camera.

These and additional objects are accomplished by the various aspects of the present invention, wherein briefly stated, one aspect is a method for positioning and orienting a camera tip (i.e., the viewing or image capturing end of the camera), the method comprising: determining positions of mechanical elements used for positioning and orienting the camera tip; determining a position and orientation of the camera tip using the determined positions of the mechanical elements; generating a view of a computer model of the camera corresponding to a perspective of a virtual camera; displaying the view on a display screen; and controlling the positioning and orienting of the camera tip by moving the mechanical elements in response to manipulation of an input device so that the positioning and orienting of the camera tip intuitively appears to an operator who is manipulating the input device while viewing the display screen to correspond to the displayed view of the computer model of the camera.

Another aspect is a medical robotic system comprising a camera, mechanical elements used for positioning and orienting a tip of the camera, a display screen, an input device, and a controller. The controller is configured to determine positions of the mechanical elements, determine a position and orientation of the camera tip using the determined positions of the mechanical elements, generate a view of a computer model of the camera corresponding to a perspective of a virtual camera, display the view on the display screen, and control the positioning and orienting of the camera tip by moving the mechanical elements in response to manipulation of the input device so that the positioning and orienting of the camera tip intuitively appears to an operator who is manipulating the input device while viewing the display screen to correspond to the displayed view of the computer model of the camera.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
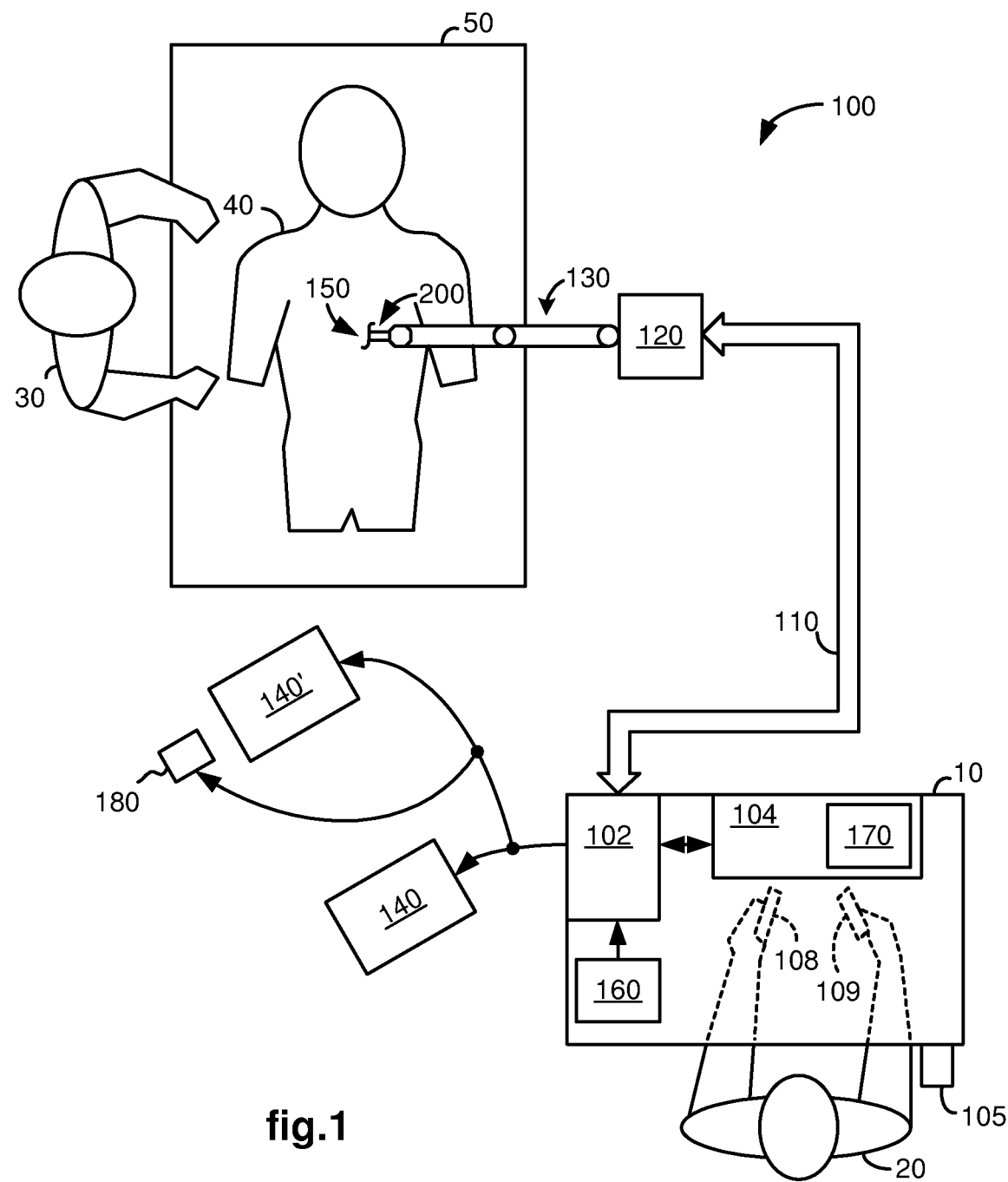
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

Figure 5:
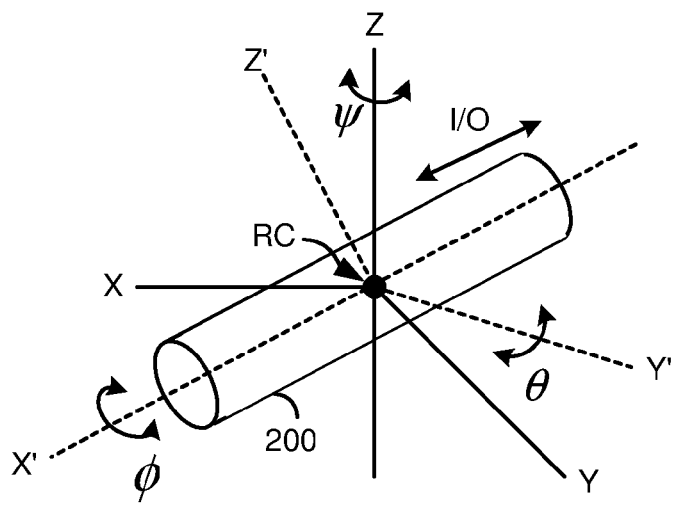
FIG. 5 illustrates a perspective view of an entry guide and its four degrees-of-freedom movement as used in a medical robotic system utilizing aspects of the present invention.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw about a pivot point located at the entry aperture 150. An example of such an entry guide manipulator is the entry guide manipulator 202 of FIG. 2 and an example of the four degrees-of-freedom movement that it manipulates the entry guide 200 with is shown in FIG. 5.

The console 10 includes a 3-D monitor 104 for displaying a 3-D image of a surgical site to the Surgeon, left and right hand-manipulatable input devices 108, 109, and a processor (also referred to herein as a "controller") 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160 and a Graphical User Interface (GUI) 170.

An auxiliary display screen 140 is coupled to the console 10 (and processor 102) for providing auxiliary views to the Surgeon to supplement those shown on the monitor 104. A second auxiliary display screen 140' is also coupled to the console 10 (and processor 102) for providing auxiliary views to the Assistant(s). An input device 180 is also coupled to the console to allow the Assistant(s) to select between available auxiliary views for display on the second auxiliary display screen 140'.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures. In such a case, the console 10 may be connected to the second auxiliary display screen 140' and input device 180 through a network connection such as a local area network, wide area network, or the Internet.

Figure 3:
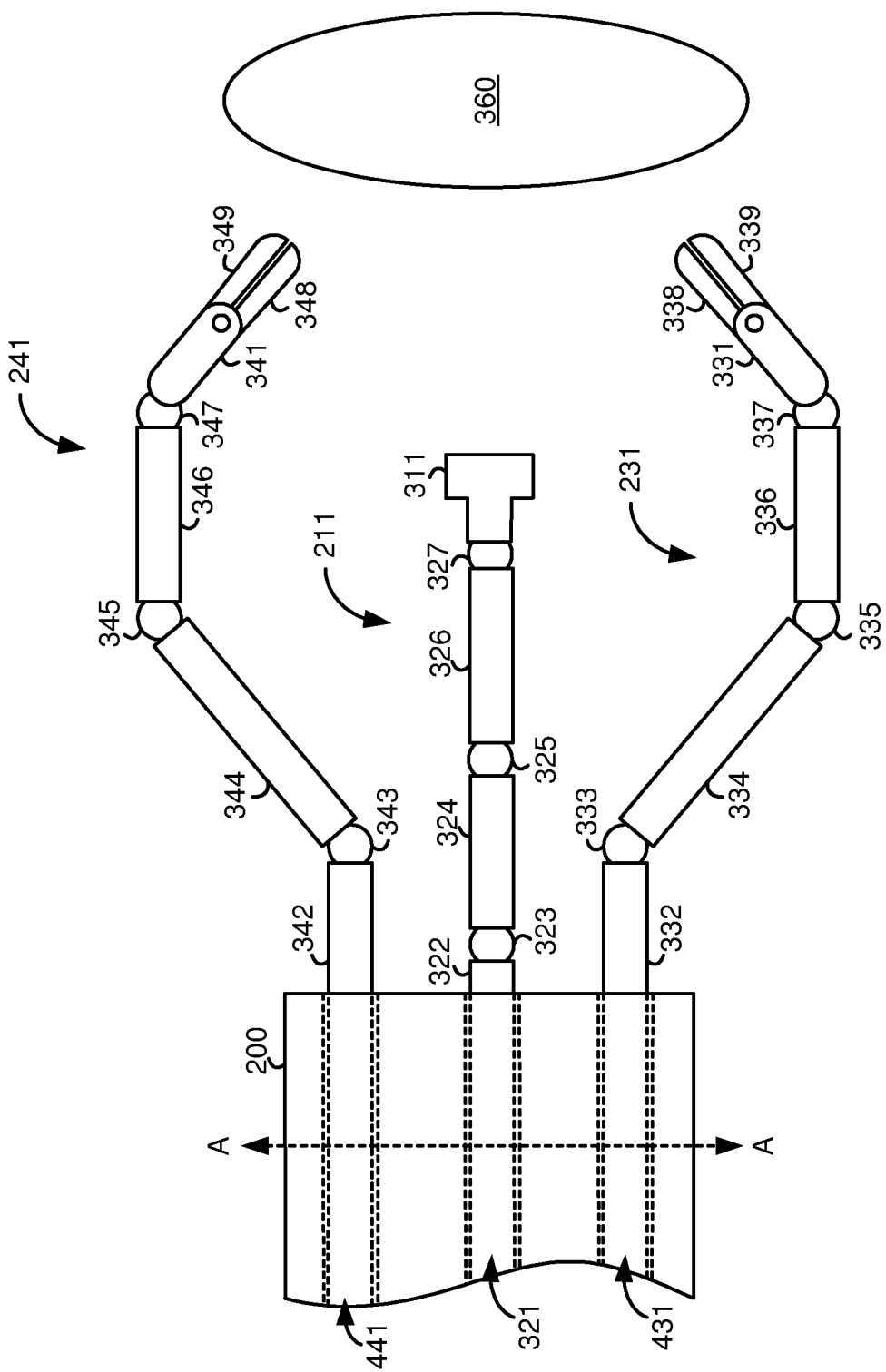
FIGS. 3-4 respectively illustrate top and side views of an articulatable camera and a pair of articulatable surgical tools extending out of a distal end of an entry guide as used in a medical robotic system utilizing aspects of the present invention.
Figure 4:
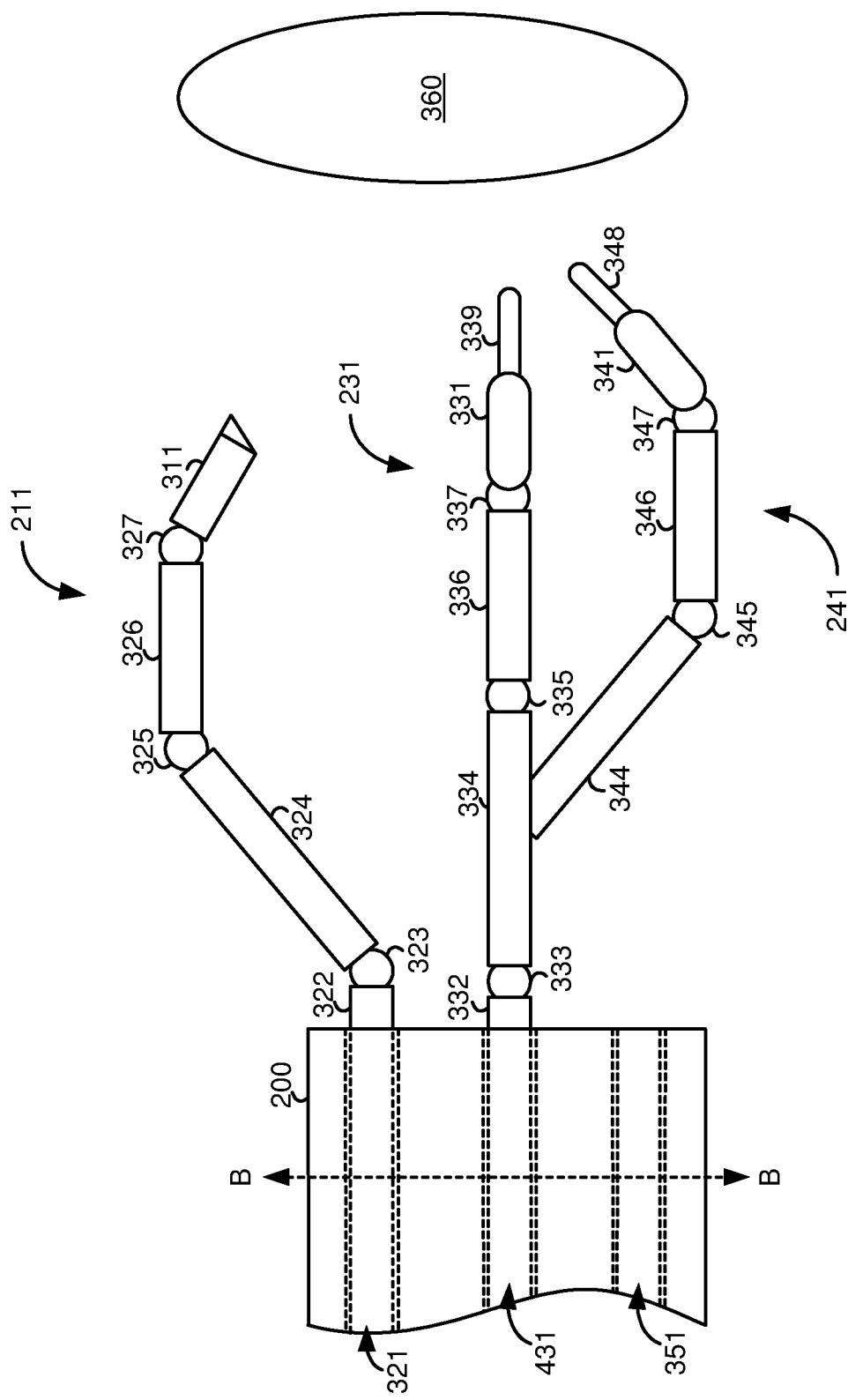

As shown in FIGS. 3-4, the entry guide 200 has articulatable instruments such as articulatable surgical tools 231, 241 and an articulatable stereo camera 211 extending out of its distal end. Although only two tools 231, 241 are shown, the entry guide 200 may guide additional tools as required for performing a medical procedure at a work site in the Patient. For example, as shown in FIG. 4, a passage 351 is available for extending another articulatable surgical tool through the entry guide 200 and out through its distal end. Each of the surgical tools 231, 241 is associated with one of the input devices 108, 109 in a tool following mode. The Surgeon performs a medical procedure by manipulating the input devices 108, 109 so that the controller 102 causes corresponding movement of their respectively associated surgical tools 231, 241 while the Surgeon views the work site in 3-D on the console monitor 104 as images of the work site are being captured by the articulatable camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 may transform the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate devices, such as the tools 231, 241, camera 211, and entry guide 200, that are selectively associated with the input devices 108, 109 at the time. Another function is to perform various methods and controller functions described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

Figure 2:
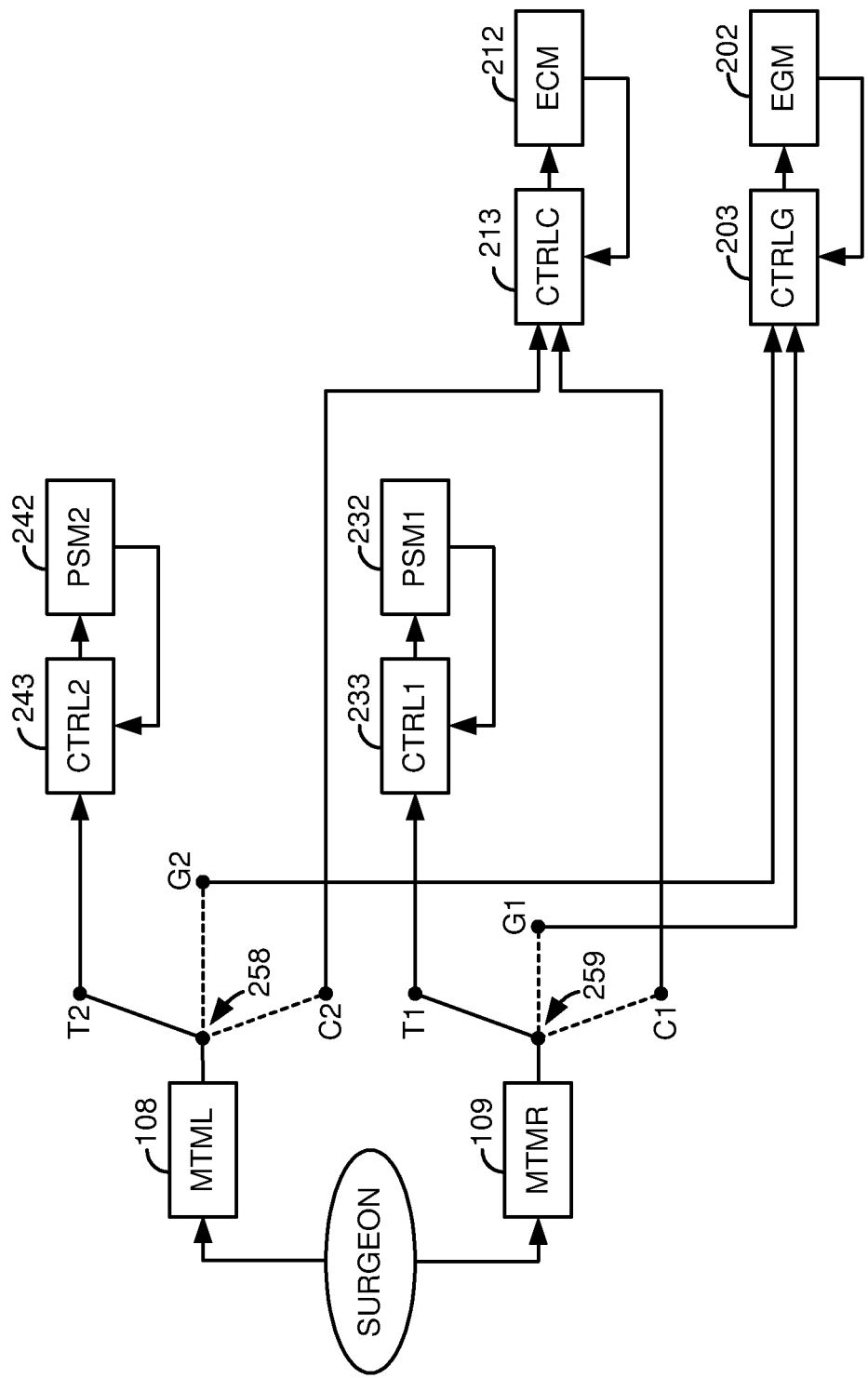
FIG. 2 illustrates a block diagram of components for controlling and selectively associating device manipulators to left and right hand-manipulatable input devices in a medical robotic system utilizing aspects of the present invention.

FIG. 2 illustrates, as an example, a block diagram of components for controlling and selectively associating device manipulators to the input devices 108, 109. Various surgical tools such as graspers, cutters, and needles may be used to perform a medical procedure at a work site within the Patient. In this example, two surgical tools 231, 241 are used to robotically perform the procedure and the camera 211 is used to view the procedure. The tools 231, 241 and camera 211 are inserted through passages in the entry guide 200. As described in reference to FIG. 1, the entry guide 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, and the entry guide 200 is manipulated by an entry guide manipulator (EGM) 202. So as to not overly encumber the figure, the devices 231, 241, 211, 200 are not shown, only their respective manipulators 232, 242, 212, 202 are shown in the figure.

Each of the instrument manipulators 232, 242, 212 is a mechanical assembly that carries actuators and provides a mechanical, sterile interface to transmit motion to its respective articulatable instrument. Each instrument 231, 241, 211 is a mechanical assembly that receives the motion from its manipulator and, by means of a cable transmission, propagates the motion to its distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams, belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

In contrast, the entry guide manipulator 202 has a different construction and operation. A description of the parts and operation of the entry guide manipulator 202 is described below in reference to FIG. 7.

In this example, each of the input devices 108, 109 may be selectively associated with one of the devices 211, 231, 241, 200 so that the associated device may be controlled by the input device through its controller and manipulator. For example, by placing switches 258, 259 respectively in tool following modes "T2" and "T1", the left and right input devices 108, 109 may be respectively associated with the first and second surgical tools 231, 241, which are telerobotically controlled through their respective controllers 233, 243 (preferably implemented in the processor 102) and manipulators 232, 242 so that the Surgeon may perform a medical procedure on the Patient while the entry guide 200 is locked in place.

When the camera 211 or the entry guide 200 is to be repositioned by the Surgeon, either one or both of the left and right input devices 108, 109 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is locked in place relative to the entry guide 200 by its controller. For example, by placing switches 258, 259 respectively in camera positioning modes "C2" and "C1", the left and right input devices 108, 109 may be associated with the camera 211, which is telerobotically controlled through its controller 213 (preferably implemented in the processor 102) and manipulator 212 so that the Surgeon may position the camera 211 while the surgical tools 231, 241 and entry guide 200 are locked in place by their respective controllers 233, 243, 203. If only one input device is to be used for positioning the camera, then only one of the switches 258, 259 is placed in its camera positioning mode while the other one of the switches 258, 259 remains in its tool following mode so that its respective input device may continue to control its associated surgical tool.

On the other hand, by placing switches 258, 259 respectively in entry guide positioning modes "G2" and "G1", the left and right input devices 108, 109 may be associated with the entry guide 200, which is telerobotically controlled through its controller 203 (preferably implemented in the processor 102) and manipulator 202 so that the Surgeon may position the entry guide 200 while the surgical tools 231, 241 and camera 211 are locked in place relative to the entry guide 200 by their respective controllers 233, 243, 213. As with the camera positioning mode, if only one input device is to be used for positioning the entry guide, then only one of the switches 258, 259 is placed in its entry guide positioning mode while the other one of the switches 258, 259 remains in its tool following mode so that its respective input device may continue to control its associated surgical tool.

The selective association of the input devices 108, 109 to other devices in this example may be performed by the Surgeon using the GUI 170 or the voice recognition system 160 in a conventional manner. Alternatively, the association of the input devices 108, 109 may be changed by the Surgeon depressing a button on one of the input devices 108, 109 or depressing the foot pedal 105, or using any other well known mode switching technique.

FIGS. 3-4 respectively illustrate, as examples, top and right side views of a distal end of the entry guide 200 with the camera 211 and surgical tools 231, 241 extending outward. As shown in a perspective view of a simplified (not to scale) entry guide 200 in FIG. 5, the entry guide 200 is generally cylindrical in shape and has a longitudinal axis X' running centrally along its length. The pivot point, which is also referred to as a remote center "RC", serves as an origin for both a fixed reference frame having X, Y and Z axes as shown and an entry guide reference frame having X', Y' and Z' axes as shown. When the system 100 is in the entry guide positioning mode, the entry guide manipulator 202 is capable of pivoting the entry guide 200 in response to movement of one or more associated input devices about the Z axis (which remains fixed in space) at the remote center "RC" in yaw $\psi$. In addition, the entry guide manipulator 202 is capable of pivoting the entry guide 200 in response to movement of the one or more input devices about the Y' axis (which is orthogonal to the longitudinal axis X' of the entry guide 200) in pitch $\theta$, capable of rotating the entry guide 200 about its longitudinal axis X' in roll $\Phi$, and linearly moving the entry guide 200 along its longitudinal axis X' in insertion/retraction or in/out "I/O" directions in response to movement of the one or more associated input devices. Note that unlike the Z-axis which is fixed in space, the X' and Y' axes move with the entry guide 200.

Figure 7:
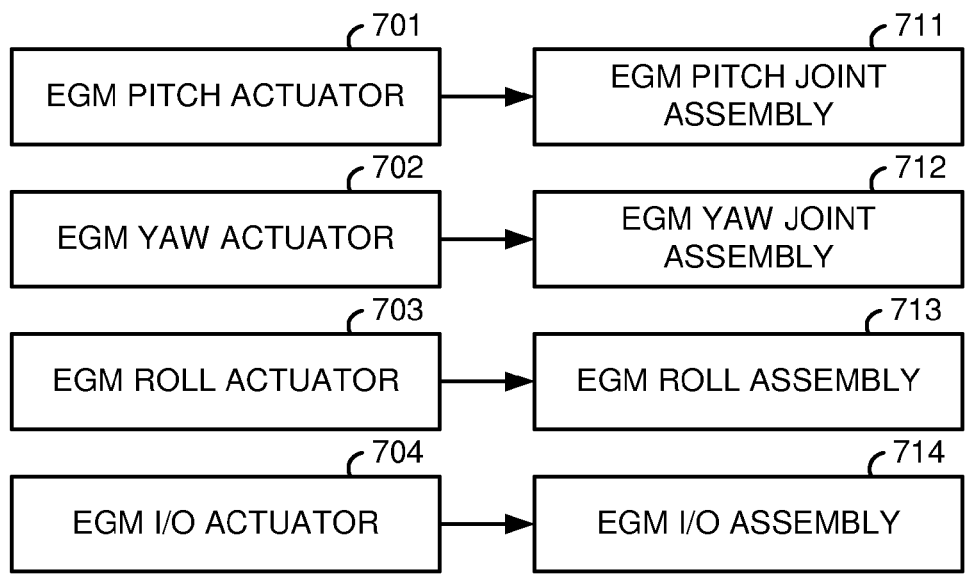
FIG. 7 illustrates a block diagram of interacting components of an entry guide manipulator as used in a medical robotic system utilizing aspects of the present invention.

As shown in FIG. 7, the entry guide manipulator (EGM) 202 has four actuators 701-704 for actuating the four degrees-of-freedom movement of the entry guide 200 (i.e., pitch $\theta$, yaw $\psi$, roll $\Phi$, and in/out I/O) and four corresponding assemblies 711-714 to implement them.

Referring back to FIGS. 3-4, the articulatable camera 211 extends through passage 321 and the articulatable surgical tools 231, 241 respectively extend through passages 431, 441 of the entry guide 200. The camera 211 includes a tip 311 (which houses a stereo camera connected to a camera controller and a fiber-optic cable connected to an external light source), first, second, and third links 322, 324, 326, first and second joint assemblies (also referred to herein simply as "joints") 323, 325, and a wrist assembly 327. The first joint assembly 323 couples the first and second links 322, 324 and the second joint assembly 325 couples the second and third links 324, 326 so that the second link 324 may pivot about the first joint assembly 323 in pitch and yaw while the first and third links 322, 326 remain parallel to each other.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal axis in roll as well as move in and out (e.g., insertion towards the work site and retraction from the worksite) through the passage 321. The wrist assembly 327 also has pitch and yaw angular movement capability so that the camera's tip 311 may be oriented up or down and to the right or left, and combinations thereof.

The joints and links of the tools 231, 241 are similar in construction and operation to those of the camera 211. In particular, the tool 231 includes an end effector 331 (having jaws 338, 339), first, second, and third links 332, 334, 336, first and second joint assemblies 333, 335, and a wrist assembly 337 that are driven by actuators such as described in reference to FIG. 8 (plus an additional actuator for actuating the end effector 331). Likewise, the tool 241 includes an end effector 341 (having jaws 348, 349), first, second, and third links 342, 344, 346, first and second joint assemblies 343, 345, and a wrist assembly 347 that are also driven by actuators such as described in reference to FIG. 8 (plus an additional actuator for actuating the end effector 341).

Figure 8:
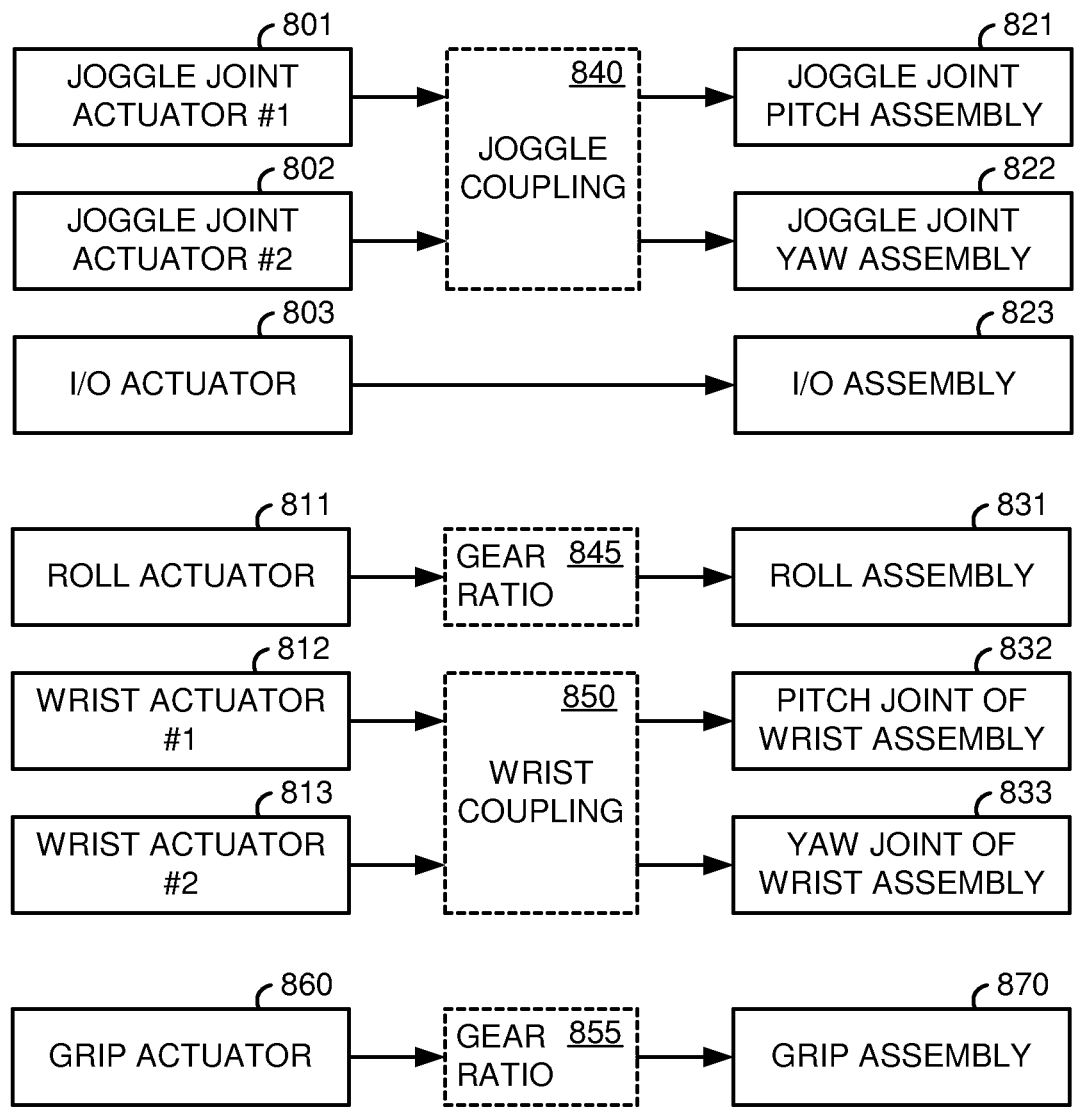
FIG. 8 illustrates a block diagram of interacting components of an articulatable instrument manipulator and an articulatable instrument as used in a medical robotic system utilizing aspects of the present invention.

FIG. 8 illustrates, as an example, a diagram of interacting parts of an articulatable instrument (such as the articulatable camera 211 and the articulatable surgical tools 231, 241) and its corresponding instrument manipulator (such as the camera manipulator 212 and the tool manipulators 232, 242). Each of the instruments includes a number of actuatable assemblies 821-823, 831-833, 870 for effectuating articulation of the instrument (including its end effector), and its corresponding manipulator includes a number of actuators 801-803, 811-813, 860 for actuating the actuatable assemblies.

In addition, a number of interface mechanisms may also be provided. For example, pitch/yaw coupling mechanisms 840, 850 (respectively for the joggle joint pitch/yaw and the wrist pitch/yaw) and gear ratios 845, 855 (respectively for the instrument roll and the end effector actuation) are provided in a sterile manipulator/instrument interface to achieve the required range of motion of the instrument joints in instrument joint space while both satisfying compactness constraints in the manipulator actuator space and preserving accurate transmissions of motion across the interface. Although shown as a single block 840, the coupling between the joggle joint actuators 801, 802 (differentiated as #1 and #2) and joggle joint pitch/yaw assemblies 821, 822 may include a pair of coupling mechanisms—one on each side of the sterile interface (i.e., one on the manipulator side of the interface and one on the instrument side of the interface). Likewise, although shown as a single block 850, the coupling between the wrist actuators 812, 813 (differentiated as #1 and #2) and wrist pitch/yaw joint assemblies 832, 833 may also comprise a pair of coupling mechanisms—one on each side of the sterile interface.

Both the joggle joint pitch assembly 821 and the joggle joint yaw assembly 822 share the first, second and third links (e.g., links 322, 324, 326 of the articulatable camera 211) and the first and second joints (e.g., joints 322, 325 of the articulatable camera 211). In addition to these shared components, the joggle joint pitch and yaw assemblies 821, 822 also include mechanical couplings that couple the first and second joints (through joggle coupling 840) to the joggle joint pitch and yaw actuators 801, 802 so that the second link may controllably pivot about a line passing through the first joint and along an axis that is latitudinal to the longitudinal axis of the first link (e.g., link 322 of the articulatable camera 211) and the second link may controllably pivot about a line passing through the first joint and along an axis that is orthogonal to both the latitudinal and longitudinal axes of the first link.

The in/out (I/O) assembly 823 includes the first link (e.g., link 322 of the articulatable camera 211) and interfaces through a drive train coupling the in/out (I/O) actuator 803 to the first link so that the first link is controllably moved linearly along its longitudinal axis by actuation of the I/O actuator 803. The roll assembly 831 includes the first link and interfaces through one or more gears (i.e., having the gear ratio 845) that couple a rotating element of the roll actuator 811 (such as a rotor of a motor) to the first link so that the first link is controllably rotated about its longitudinal axis by actuation of the roll actuator 811.

The instrument manipulator (e.g., camera manipulator 212) includes wrist actuators 812, 813 that actuate through wrist coupling 850 pitch and yaw joints 832, 833 of the wrist assembly (e.g., wrist 327 of the articulatable camera 211) so as to cause the instrument tip (e.g., camera tip 311) to controllably pivot in an up-down (i.e., pitch) and side-to-side (i.e., yaw) directions relative to the wrist assembly. The grip assembly 870 includes the end effector (e.g., end effector 331 of the surgical tool 231) and interfaces through one or more gears (i.e., having the gear ratio 855) that couple the grip actuator 860 to the end effector so as to controllably actuate the end effector.

Figure 9:
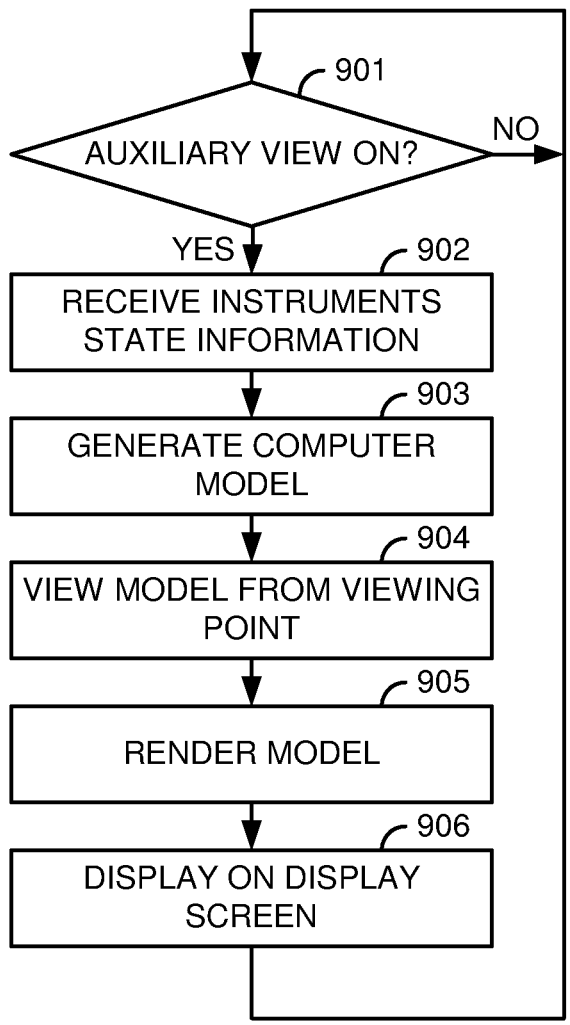
FIG. 9 illustrates a flow diagram of a method for providing a computer generated auxiliary view, utilizing aspects of the present invention.

FIG. 9 illustrates, as an example, a flow diagram of a method implemented in controller 102 of the medical robotic system 100 for providing a computer generated auxiliary view including articulatable instruments, such as the articulatable camera 211 and/or one or more of the articulatable surgical tools 231, 241, extending out of the distal end of the entry guide 200. For the purposes of this example, it is assumed that the articulatable camera 211 and surgical tools 231, 241 extend out of the distal end of the entry guide 200 and are included in the auxiliary view. However, it is to be appreciated that the method is applicable to any combination of articulatable instruments, including those without an articulatable camera and/or those with an alternative type of image capturing device such as an ultrasound probe.

In 901, the method determines whether or not an auxiliary view is to be generated. If the determination in 901 is NO, then the method loops back to periodically check to see whether the situation has changed. On the other hand, if the determination in 901 is YES, then the method proceeds to 902. The indication that an auxiliary view is to be generated may be programmed into the controller 102, created automatically or created by operator command.

In 902, the method receives state information, such as positions and orientations, for each of the instruments 211, 231, 241 and the entry guide 200. This information may be provided by encoders coupled to the actuators in their respective manipulators 212, 232, 242, 202. Alternatively, the information may be provided by sensors coupled to joints and/or links of the instruments 211, 231, 241 and the entry guide manipulator 202, or the coupling mechanisms, gears and drive trains of the interface between corresponding manipulators and instruments, so as to measure their movement. In this second case, the sensors may be included in the instruments 211, 231, 241 and entry guide manipulator 202 such as rotation sensors that sense rotational movement of rotary joints and linear sensors that sense linear movement of prismatic joints in the instruments 211, 231, 241 and entry guide manipulator 202. Other sensors may also be used for providing information of the positions and orientations of the instruments 211, 231, 241 and entry guide 200 such as external sensors that sense and track trackable elements, which may be active elements (e.g., radio frequency, electromagnetic, etc.) or passive elements (e.g., magnetic, etc.), placed at strategic points on the instruments 211, 231, 241, the entry guide 200 and/or the entry guide manipulator 202 (such as on their joints, links and/or tips).

In 903, the method generates a three-dimensional computer model of the articulatable camera 211 and articulatable surgical tools 231, 241 extending out of the distal end of the entry guide 200 using the information received in 902 and the forward kinematics and known constructions of the instruments 211, 231, 241, entry guide 200, and entry guide manipulator 202. The generated computer model in this example may be referenced to the remote center reference frame (X, Y, Z axes) depicted in FIG. 5. Alternatively, the generated computer model may be referenced to a reference frame defined at the distal end of the entry guide 200. In this latter case, if the orientation and extension of the entry guide 200 from the remote center does not have to be accounted for in the auxiliary view that is being generated by the method, then the position and orientation information for the entry guide 200 may be omitted in 902.

Figure 10:
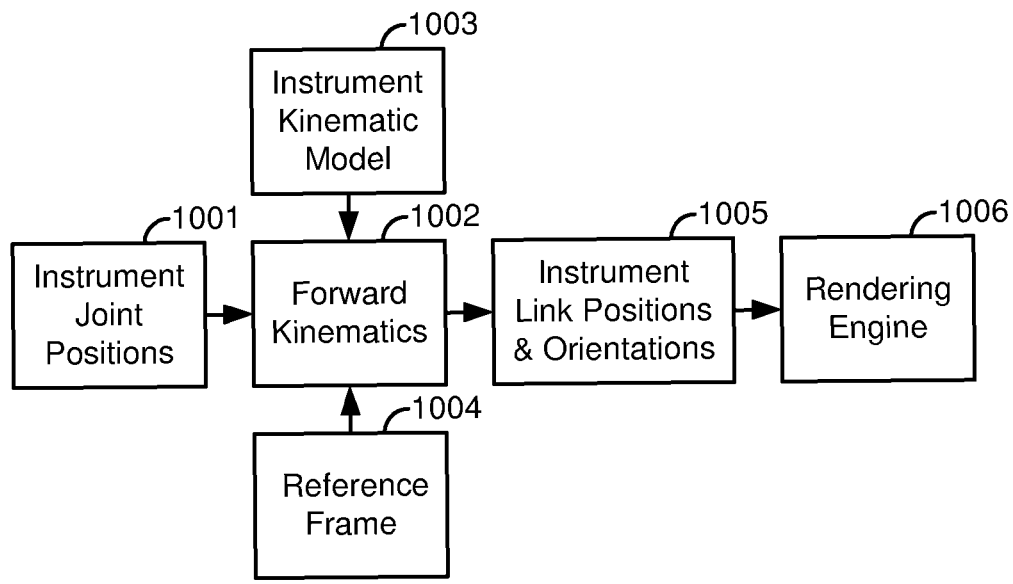
FIG. 10 illustrates a data and processing flow diagram to determine instrument link positions and orientations using instrument joint positions and forward kinematics, as used in a medical robotic system utilizing aspects of the present invention.

For example, referring to FIG. 10, if the state information received in 902 is the instruments' joint positions 1001, then this information may be applied to the instruments' forward kinematics 1002 using the instruments' kinematic models 1003 to generate the instruments' link positions and orientations 1005 relative to reference frame 1004. The same process may also be generally applied if the state information received in 902 is sensed states of the joggle coupling and gear mechanisms in the manipulator/instrument interfaces.

Figure 11:
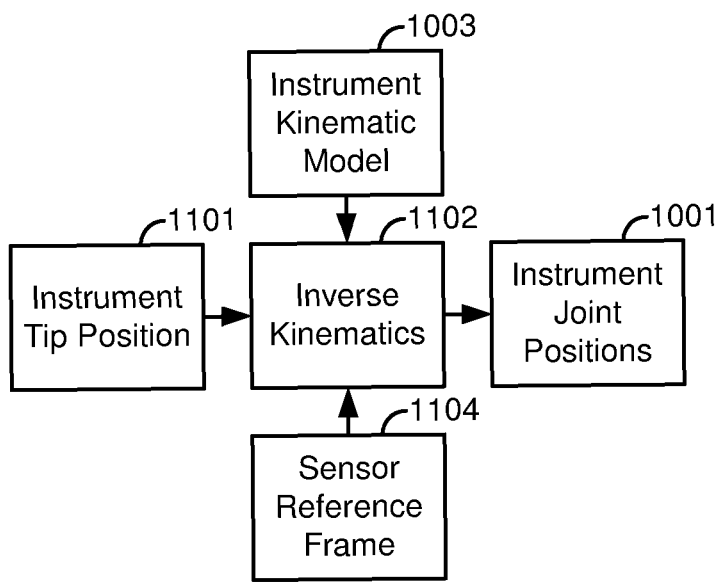
FIG. 11 illustrates a data and processing flow diagram to determine instrument joint positions using a sensed instrument tip position and inverse kinematics, as used in a medical robotic system utilizing aspects of the present invention.

On the other hand, referring to FIG. 11, if the state information received in 902 is the instruments' tip positions 1101 (in the reference frame 1004), then this information may be applied to the instruments' inverse kinematics 1102 using the instruments' kinematic models 1003 and the sensor reference frame to generate the instruments' joint positions 1001. The instruments' joint positions 1001 may then be applied as described in reference to FIG. 10 to generate the instruments' link positions and orientations 1005 relative to reference frame 1004.

Alternatively, also referring to FIG. 11, if the state information provided in 902 is limited to only the camera's tip position, then the positions of the tips of the surgical tools 231, 241 may be determined relative to the camera reference frame by identifying the tips in the image captured by the camera 211 using conventional image processing techniques and then translating their positions to the reference frame 1004, so that the positions of the camera and tool tips may be applied as described in reference to FIGS. 10, 11 to generate the instruments' link positions and orientations 1005 relative to the reference frame 1004.

Figure 12:
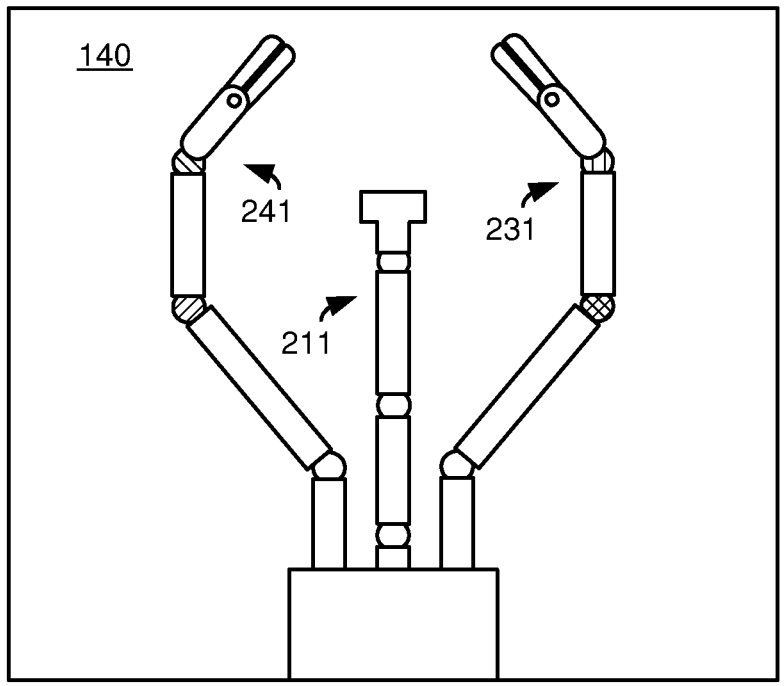
FIGS. 12-13 respectively illustrate top and side auxiliary views as generated and displayed on a display screen by a method implemented in a medical robotic system utilizing aspects of the present invention.
Figure 13:
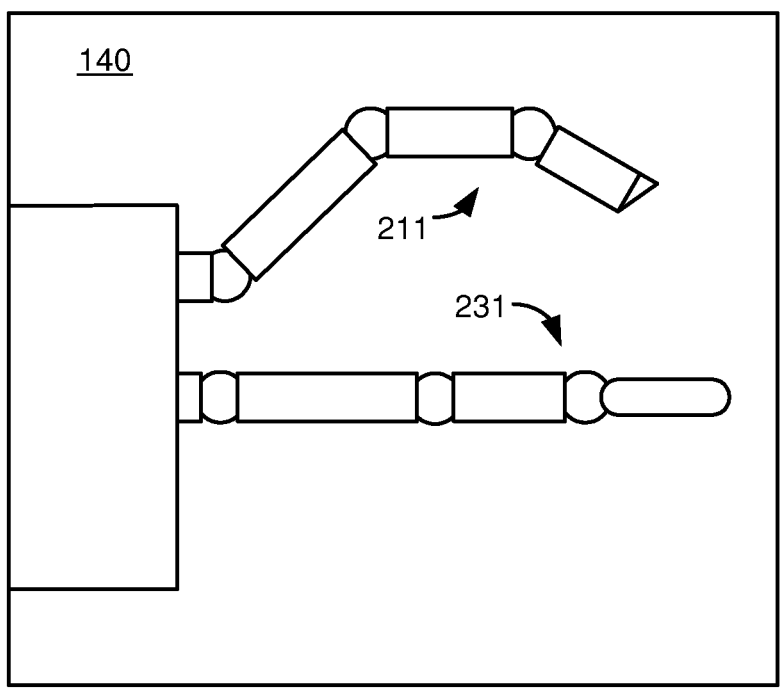

In 904, the method adjusts the view of the computer model of the articulatable camera 211 and articulatable surgical tools 231, 241 extending out of the distal end of the entry guide 200 in the three-dimensional space of the reference frame to a specified viewing point (wherein the term "viewing point" is to be understood herein to include position and orientation). For example, FIG. 12 illustrates a top view of the articulatable camera 211 and articulatable surgical tools 231, 241 extending out of the distal end of the entry guide 200 which corresponds to a viewing point above and slightly behind the distal end of the entry guide 200. As another example, FIG. 13 illustrates a side view of the articulatable camera 211 and articulatable surgical tools 231, 241 extending out of the distal end of the entry guide 200 which corresponds to a viewing point to the right and slightly in front of the distal end of the entry guide 200. Note that although the auxiliary views depicted in FIGS. 12-13 are two-dimensional, they may also be three-dimensional views since three-dimensional information is available from the generated computer model. In this latter case, the auxiliary display screen 140 that they are being displayed on would have to be a three-dimensional display screen like the monitor 104.

Figure 6:
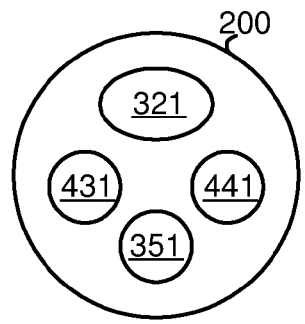
FIG. 6 illustrates a cross-sectional view of an entry guide with passages defined therein that extend between its proximal and distal ends as used in a medical robotic system utilizing aspects of the present invention.

The viewing point may be set at a fixed point such as one providing an isometric (three-dimensional) view from the perspective shown in FIG. 12. This perspective provides a clear view to the surgeon of the articulatable camera 211 and the articulatable surgical tools 231, 241 when the tools 231, 241 are bent "elbows out" as shown (which is a typical configuration for performing a medical procedure using the surgical tools 231, 241). On the other hand, when a third surgical tool is being used (e.g., inserted in the passage 351 shown in FIG. 6), a side view from the perspective of FIG. 13 may additionally be useful since the third surgical tool may be beneath the articulatable camera 211 and therefore obscured by it in the perspective shown in FIG. 12.

Figure 16:
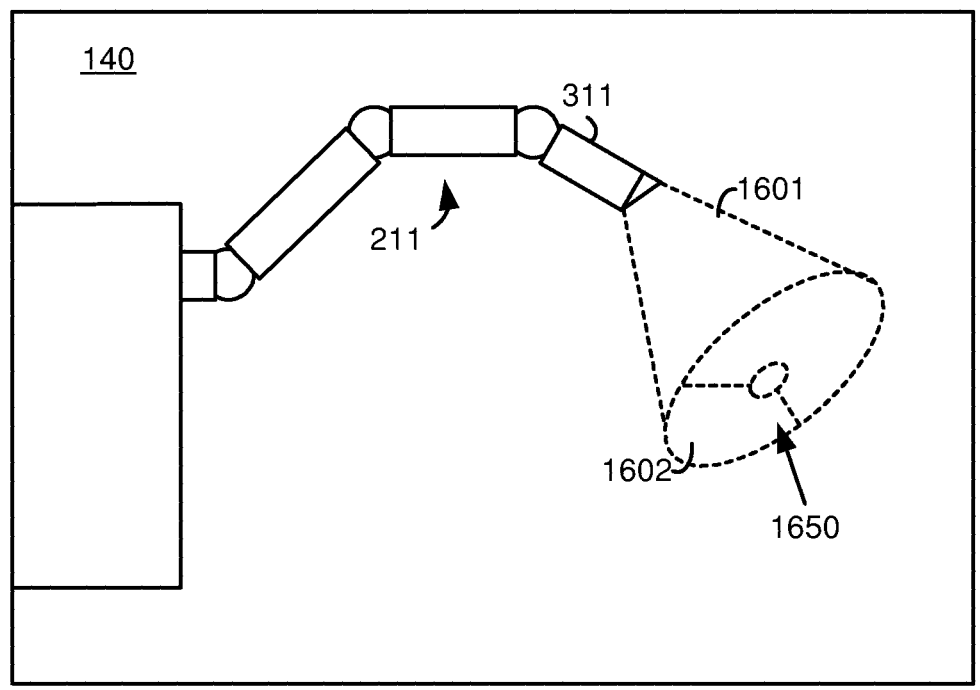
FIG. 16 illustrates an auxiliary side view of an articulatable camera having a frustum as generated and displayed by a method implemented in a medical robotic system utilizing aspects of the present invention on a display screen.
Figure 17:
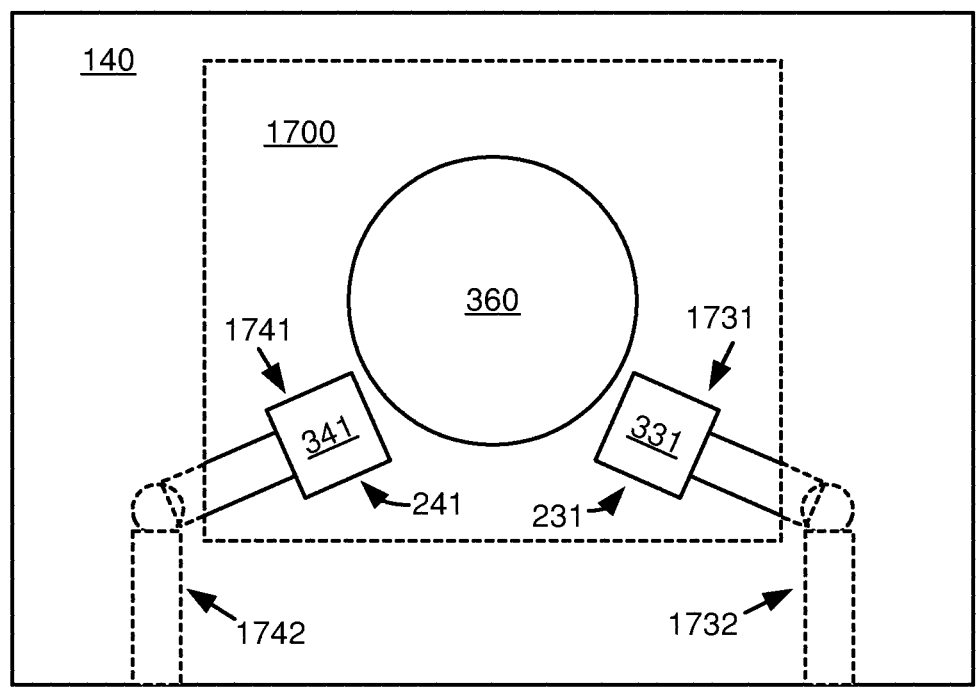
FIG. 17 illustrates a combined display of an auxiliary view of a pair of articulatable surgical tools from a viewing point of a camera, along with an image captured by the camera, as generated and displayed by a method implemented in a medical robotic system utilizing aspects of the present invention on a display screen.
Figure 18:
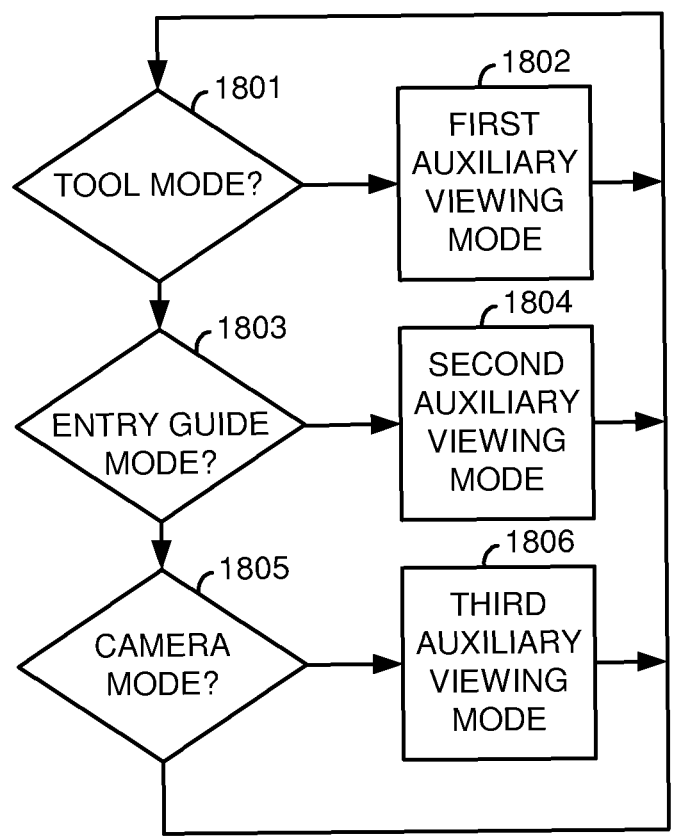
FIG. 18 illustrates a flow diagram of a method for providing auxiliary viewing modes that correspond to device control modes in a medical robotic system, utilizing aspects of the present invention.

Rather than setting the viewing point to a fixed point at all times, the viewing point may also be automatically changed depending upon the control mode (i.e., one of the modes described in reference to FIG. 2) that is operative at the time. As an example, FIG. 18 illustrates a method for automatically changing the auxiliary viewing mode depending upon the control mode currently operative in the medical robotic system 100. In particular, using this method, a first auxiliary viewing mode is performed in 1802 when the medical robotic system 100 is determined in 1801 to be in a tool following mode, a second auxiliary viewing mode is performed in 1804 when the medical robotic system 100 is determined in 1803 to be in an entry guide positioning mode, and a third auxiliary viewing mode is performed in 1806 when the medical robotic system 100 is determined in 1805 to be in a camera positioning mode. The viewing modes for each control mode are selected so as to be most beneficial to the surgeon for performing actions during that mode. For example, in the tool following and camera positioning modes, either or both the surgical tools 231, 241 and camera 211 is being moved at the time and therefore, an auxiliary view of the articulatable camera 211 and articulatable surgical tools 231, 241 extending out of the distal end of the entry guide 200, such as depicted in FIGS. 12 and 13, is useful to avoid collisions between links that are out of the field of view of the camera 211. On the other hand, in the entry guide positioning mode, the articulatable camera 211 and the articulatable surgical tools 231, 241 are locked in position relative to the entry guide 200 and therefore, an auxiliary view providing information on other things such as depicted in FIGS. 16 and 17 may be useful.

Alternatively, operator selectable means for changing the viewing point during the performance of a medical procedure may be provided. For example, the GUI 170 or voice recognition system 160 may be adapted to provide an interactive means for the Surgeon to select the viewing mode and/or change the viewing point of an auxiliary view of the articulatable camera 211 and/or articulatable surgical tools 231, 241 as they extend out of the distal end of the entry guide 200. Buttons on the input devices 108, 109 or the foot pedal 105 may also be used for Surgeon selection of viewing modes. For the Assistant(s), the input device 180 may be used along with a GUI associated with the display screen 140' for selection of viewing modes. Thus, the viewing modes that the Surgeon and Assistant(s) see at the time may be optimized for their particular tasks at the time. Examples of such operator selectable viewing modes and viewing angles are depicted in FIGS. 12-17.

In 905, the method renders the computer model. Rendering in this case includes adding three-dimensional qualities such as known construction features of the instruments 211, 231, 241 and the distal end of the entry guide 200 to the model, filling-in any gaps to make solid models, and providing natural coloring and shading. In addition, rendering may include altering the color or intensity of one or more of the instruments 211, 231, 241 (or one or more of their joints or links or portions thereof) so that the instrument (or joint or link or portion thereof) stands out for identification purposes.

Alternatively, the altering of the color, intensity, or frequency of blinking on and off (e.g., flashing) of one or more of the instruments 211, 231, 241 (or their joints, links, or portions thereof) may serve as a warning that the instrument (or joint or link or portion thereof) is approaching an undesirable event or condition such as nearing a limit of its range of motion or getting too close to or colliding with another one of the instruments. When color is used as a warning, the color may go from a first color (e.g., green) to a second color (e.g., yellow) when a warning threshold of an event to be avoided (e.g., range of motion limitation or collision) is reached, and from the second color to a third color (e.g., red) when the event to be avoided is reached. When intensity is used as a warning, the intensity of the color changes as the instrument (or portion thereof) moves past the warning threshold towards the event to be avoided with a maximum intensity provided when the event is reached. When blinking of the color is used as a warning, the frequency of blinking changes as the instrument (or portion thereof) moves past the warning threshold towards the event to be avoided with a maximum frequency provided when the event is reached. The warning threshold may be based upon a range of motion of the instrument (or portion thereof, such as its joints) or upon a distance between the instrument (or portion thereof) and another instrument (or portion thereof) that it may collide with. Velocity of the instrument's movement may also be a factor in determining the warning threshold. The warning threshold may be programmed by the operator, using the GUI 170, for example, or determined automatically by a programmed algorithm in the processor 102 that takes into account other factors such as the velocity of the instruments' movements.

Alternatively, the altering of the color, intensity, or frequency of blinking on and off (e.g., flashing) of one or more of the instruments 211, 231, 241 (or their joints, links, or portions thereof) may serve as an alert that the instrument (or joint or link or portion thereof) is approaching a desirable event or condition such as an optimal position or configuration for performing or viewing a medical procedure. In this case, an alert threshold may be defined so that the color, intensity, and/or blinking of the one or more of the instruments 211, 231, 241 (or their joints, links, or portions thereof) may change in a similar manner as described previously with respect to warning thresholds and undesirable events or conditions, except that in this case, the change starts when the alert threshold is reached and maximizes or otherwise ends when the desirable event or condition is reached or otherwise achieved. The alert threshold may also be programmed by the operator or determined automatically by a programmed algorithm in a conceptually similar manner as the warning threshold.

Figure 14:
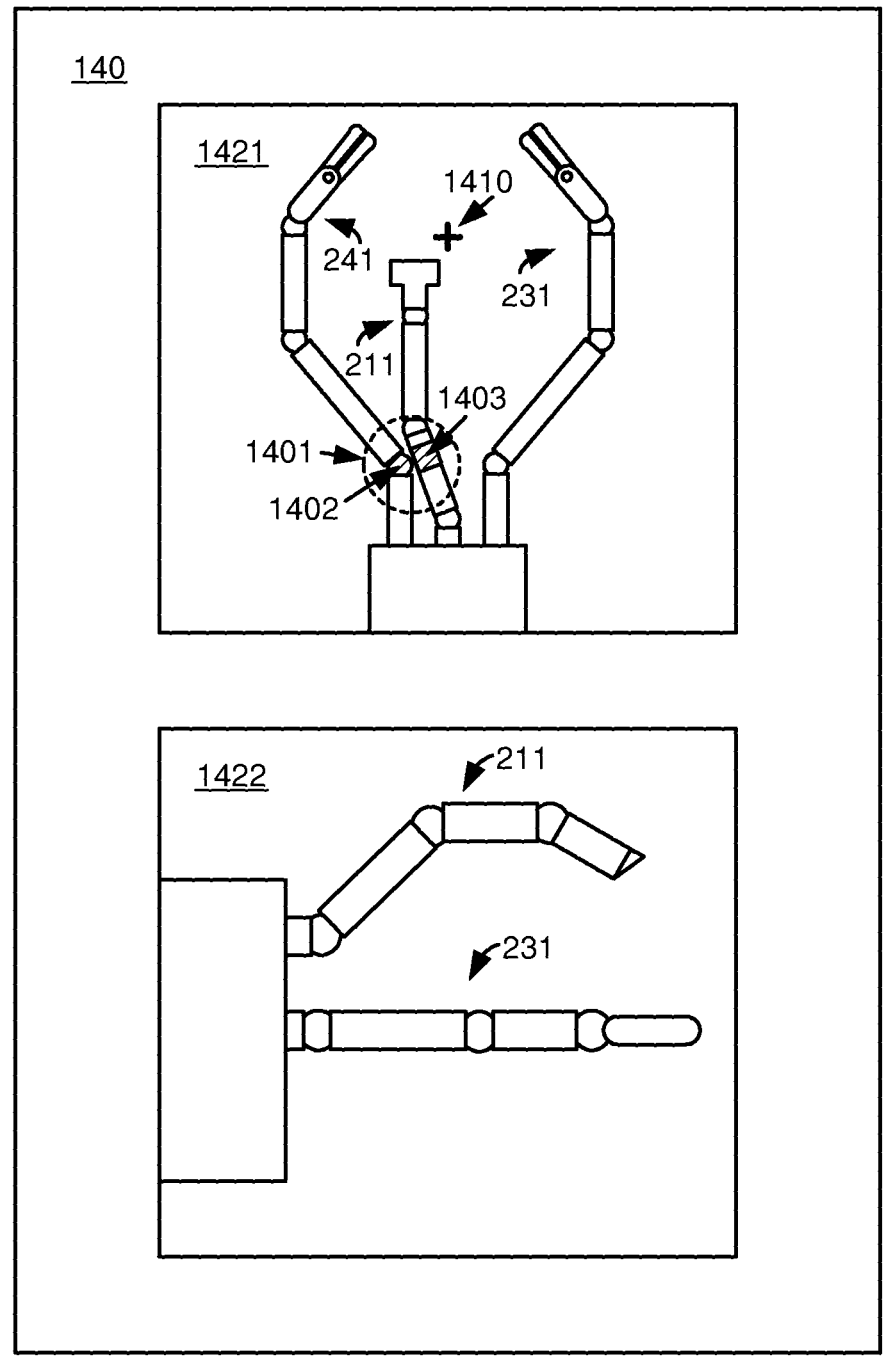
FIG. 14 illustrates top and side auxiliary views as generated and displayed in separate windows on a display screen by a method implemented in a medical robotic system utilizing aspects of the present invention.
Figure 15:
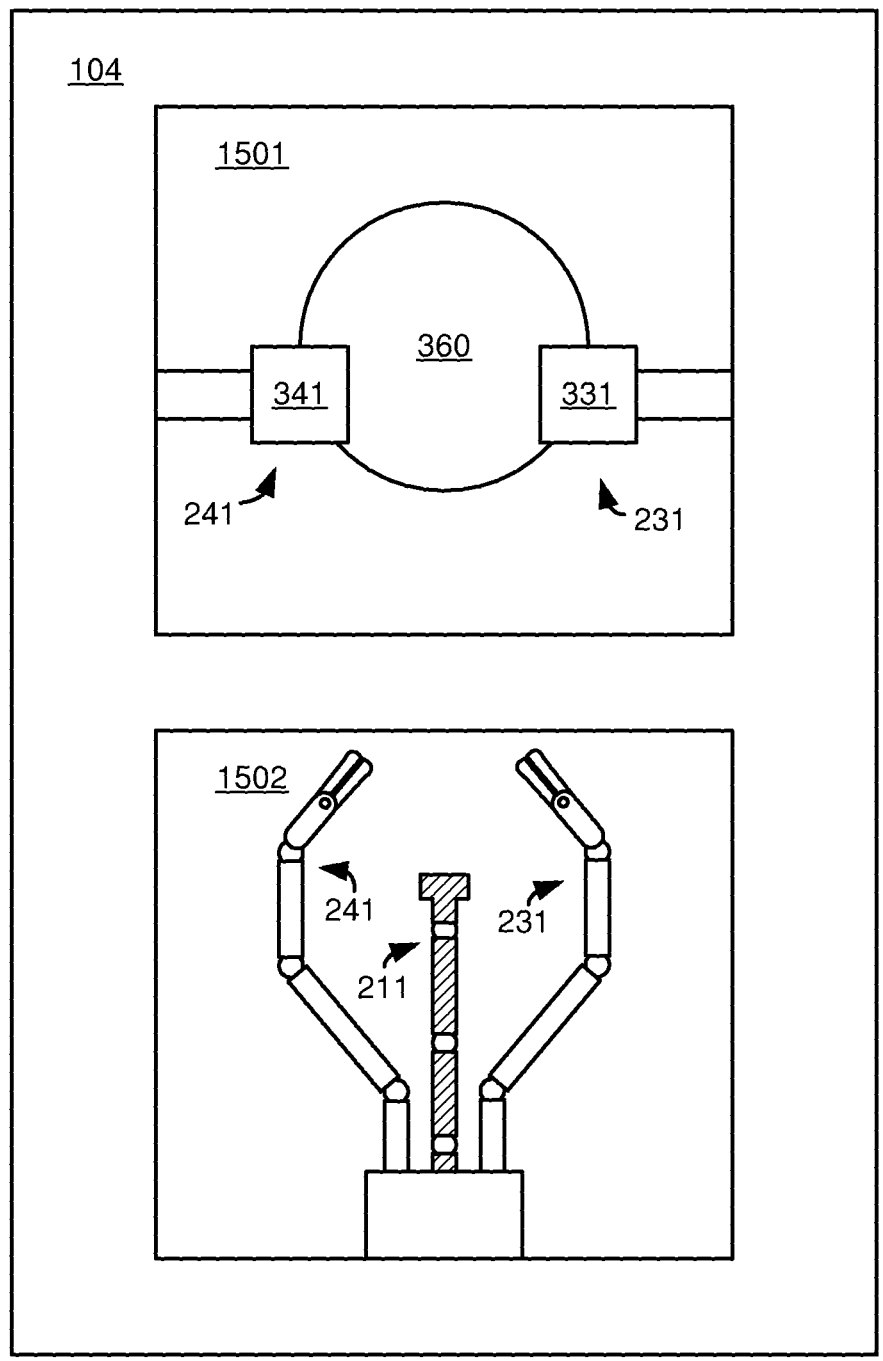
FIG. 15 illustrates an auxiliary view displayed adjacent to an image captured by the articulatable camera on a monitor in a medical robotic system utilizing aspects of the present invention.

As an example of such highlighting of an instrument for identification, warning or alerting purposes, FIG. 15 shows an auxiliary view of the camera 211 and surgical tools 231, 241 in a window 1502, where the camera 211 has been highlighted. As an example of such highlighting of joints of instruments for identification, warning or alerting purposes, FIG. 12 shows joints of the surgical tools 231, 241 that have been highlighted. As an example of highlighting portions of instruments for warning purposes, FIG. 14 shows a portion 1402 of the surgical tool 241 and a portion 1403 of the camera 211 highlighted to indicate that these portions are dangerously close to colliding.

Rendering may also include overlaying the image captured by the camera 211 over the auxiliary view when the viewing point of the auxiliary image is the same as or directly behind that of the camera 211. As an example, FIG. 17 illustrates a captured image 1700 of the camera 211 rendered as an overlay to an auxiliary view of surgical tools 231, 241 which has been generated from a viewing point of (or right behind) the camera 211. In this example, the auxiliary view of the surgical tools 231, 241 being displayed on the auxiliary display screen 140 (and/or the auxiliary display screen 140') includes portions (e.g., 1731, 1741) in the overlaying captured image 1700 and portions (e.g., 1732, 1742) outside of the overlaying captured image 1700. Thus, the portions of the surgical tools 231, 241 outside of the captured image 1700 provide the Surgeon with additional information about their respective links or articulating arms that are out of the field of view of the camera 211. Highlighting of the instrument portions (e.g., 1732, 1742) outside of the captured image 1700 may also be done for identification purposes or to indicate a warning or alerting condition as described above. Overlaying the captured image 1700 onto the auxiliary view also has the advantage in this case of showing an anatomic structure 360 which is in front of the surgical tools 231, 241 that would not otherwise normally be in the auxiliary view. Although this example shows the captured image 1700 overlaying the auxiliary view on the auxiliary display screen 140, in another rendering scheme, the auxiliary view may overlay the captured image that is being displayed on the monitor 104.

Rather than overlaying the captured image, rendering may also include using the auxiliary view to augment the image captured by the camera 211 by displaying only the portions of the instruments 231, 241 that are not seen in the captured image (i.e., the dotted line portion of the instruments 231, 241 in FIG. 17) in proper alignment and adjacent the captured image in a mosaic fashion.

In addition to, or in lieu of, overlaying the captured image over the auxiliary view or augmenting the captured image with the auxiliary view, rendering may also include providing other useful information in the auxiliary view. As an example, FIG. 16 illustrates an auxiliary side view of an articulatable camera 211 with a frustum 1601 rendered on the auxiliary view so as to be displayed on the auxiliary display 140 as emanating from, and moving with, the camera tip 311. Note that although the frustum 1601 is shown in the figure as a truncated cone, it may also appear as a truncated pyramid to correspond to the captured image that is shown on the monitor 104. The sides of the frustum 1601 indicate a viewing range of the camera 211 and the base 1602 of the frustum 1601 displays an image 1650 that was captured by the camera 211. Note that for simplification purposes, the surgical tools 231, 241 normally in the auxiliary view have been removed for this example. As another example, FIG. 14 shows a semi-translucent sphere or bubble 1401 (preferably colored red) which is displayed by the method as part of the rendering process when a warning threshold is reached so as to indicate to the operator that the highlighted portions 1402, 1403 of the surgical tool 241 and camera 211 are dangerously close to colliding. In this case, the highlighted portions 1402, 1403 are preferably centered within the sphere. As yet another example, FIG. 14 also shows a marker or other indicator 1410 indicating an optimal position for the camera tip 311 for viewing the end effectors of the surgical tools 231, 241 as they are being used to perform a medical procedure. The optimal position may be determined, for example, by finding a location where the tips of the end effectors are equidistant from a center of the captured image.

In 906, the method causes the rendered computer model (i.e., the auxiliary view) to be displayed on one or more displayed screens (e.g., 140 and 140') from the perspective of the selected viewing point. As shown in FIGS. 12-14 and 16-17, the auxiliary view is displayed on the auxiliary display screen 140. As shown in FIG. 14, more than one auxiliary view may be displayed at one time (e.g., top and side perspectives may be provided at the same time respectively in windows 1421 and 1422). As shown in FIG. 15, the auxiliary view may also be displayed on the primary monitor 104 in a window 1502 that is adjacent to an image captured by the articulatable camera 211 which is being shown in another window 1501. Although the windows 1501 and 1502 appear in this example to be the same size, it is to be appreciated that the position and size of the auxiliary view window 1502 may vary and still be within the scope of the present invention. Also, as previously mentioned, the auxiliary view may be overlayed the captured image in the window 1501 instead of in its own separate window 1502. In such case, the overlayed auxiliary view may be switched on and off by the Surgeon so as not to clutter the captured image during the performance of a medical procedure. The switching on and off in this case may be performed by depressing a button on one of the input devices 108, 109 or depressing the foot pedal 105. Alternatively, it may be done by voice activation using the voice recognition system 160 or through Surgeon interaction with the GUI 170 or using any other conventional function switching means.

After completing 906, the method then loops back to 901 to repeat 901-906 for the next processing cycle of the controller 102.

When the Surgeon desires to reposition the camera tip 311 to a more advantageous position and/or orientation to view a medical procedure being or to be performed at a work site in the Patient, one or both of the input devices 108, 109 may be used to do so by temporarily associating it/them with the camera manipulator 212. One way that the Surgeon may perform such repositioning is for him or her to view images on the 3-D monitor 104 that were captured by the stereoscopic camera in the camera tip 311, such as the image shown in window 1501 of FIG. 15, and use the captured images to guide his or her manipulation of the input device. This type of camera control is referred to as "image referenced control" since the Surgeon uses the image captured by the camera 211 as a reference for his or her controlling of the camera movement (i.e., the motion of the input device 108 corresponds to the motion of the camera tip 311 with respect to the captured image). Although image referenced control may be useful when the Surgeon is fine tuning the position and/or orientation of the camera tip 311, for larger movements problems may occur as a result of unintentional collisions between instrument links outside the field of view of the camera 211. In this latter case, an "instrument referenced control" may be more desirable where an auxiliary image of the camera 211 and tools 231, 241 extending out of the distal end of the entry guide 200, such as shown in window 1502 of FIG. 15, may be preferable for guiding the Surgeon's manipulation of the input device (i.e., the motion of the input device 108 corresponds to the motion of the camera tip 311 with respect to the auxiliary image).

Figure 19:
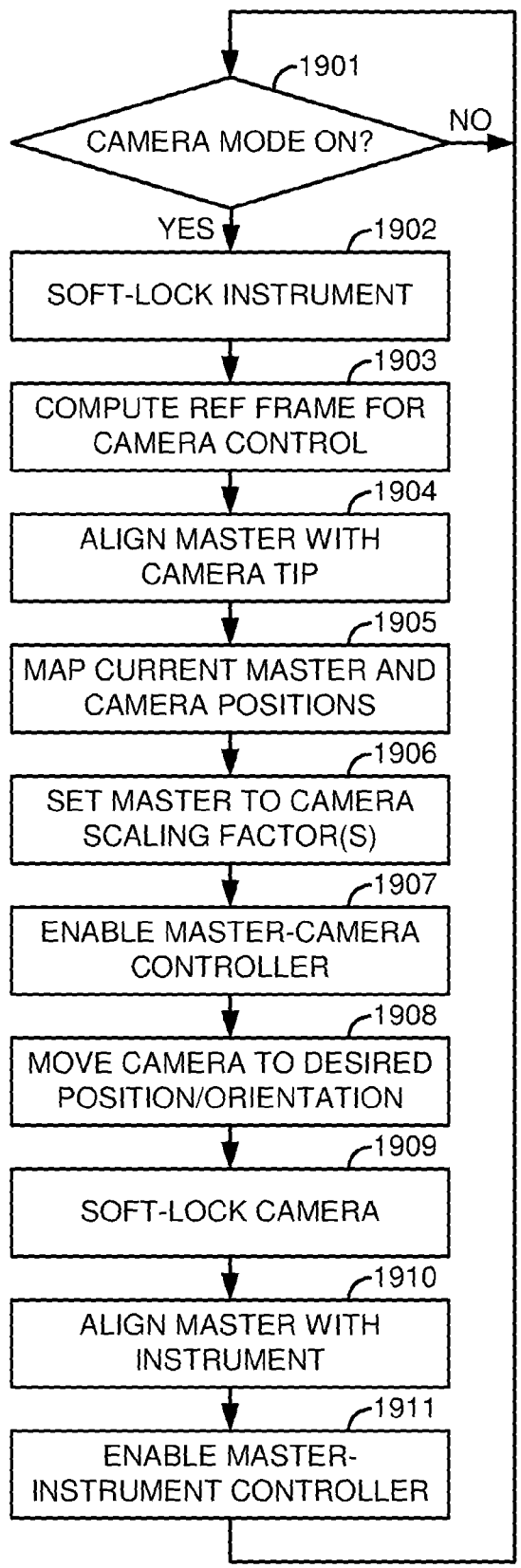
FIG. 19 illustrates a flow diagram of a method for positioning and orienting a camera tip utilizing aspects of the present invention.

FIG. 19 illustrates, as an example of "instrument referenced control", a flow diagram of a method implemented in the medical robotic system 100 for positioning and orienting the tip 311 of the articulatable camera instrument 211 in response to operator manipulation of the input device 108 (in camera positioning mode) while the operator views a computer generated auxiliary view of the camera 211 on either the display screen 140 or the console monitor 104. Although both input devices 108, 109 may be used for positioning and orienting the camera 211, such as a bicycle "handlebar" type control, the present example assumes that only one input device 108 (also referred to herein as the "master" or "master manipulator") is used so that the other input device 109 may still be associated with and control its tool 231.

In 1901, a determination is made whether the medical robotic system is in camera positioning mode. As previously described in reference to FIG. 2, this may be determined for the left input device 108 by checking the state of its switch 258. If the switch 258 is in the "C2" position, then the input device 108 is in camera positioning mode. Otherwise, the input device 108 is not in camera positioning mode.

If the determination in 1901 is NO, then the method periodically loops back (e.g., at each processing cycle or a programmable multiple of a processing cycle) to check the current status of the switch 258. On the other hand, if the determination in 1901 is YES, then the method performs preparatory tasks 1902-1906 before enabling control over the positioning and orienting of the camera tip 311 by the input device 108 in 1907.

In 1902, the other medical devices 241, 200 associated with the input device 108 are soft-locked so that they are commanded to remain in their present stationary state by their controllers 242, 202.

In 1903, the method computes the reference frame which is used for control purposes (the "control reference frame"). This reference frame is necessary to map between the Cartesian motion of the master 108 and the Cartesian motion of the camera tip 311. The reference frame is preferably fixed in space during camera positioning mode for ease of computation. Thus, a reference frame defined by the camera tip 311, such as in tool following mode, is not desirable in camera positioning mode because in camera positioning mode, the camera tip 311 is moving and therefore, even though its state is determinable, its pose is not clearly perceivable by the Surgeon. Therefore, the Surgeon may find it more difficult in this situation to position the camera tip 311 at the desired location with respect to the Patient's anatomy using the master 108.

Figure 20:
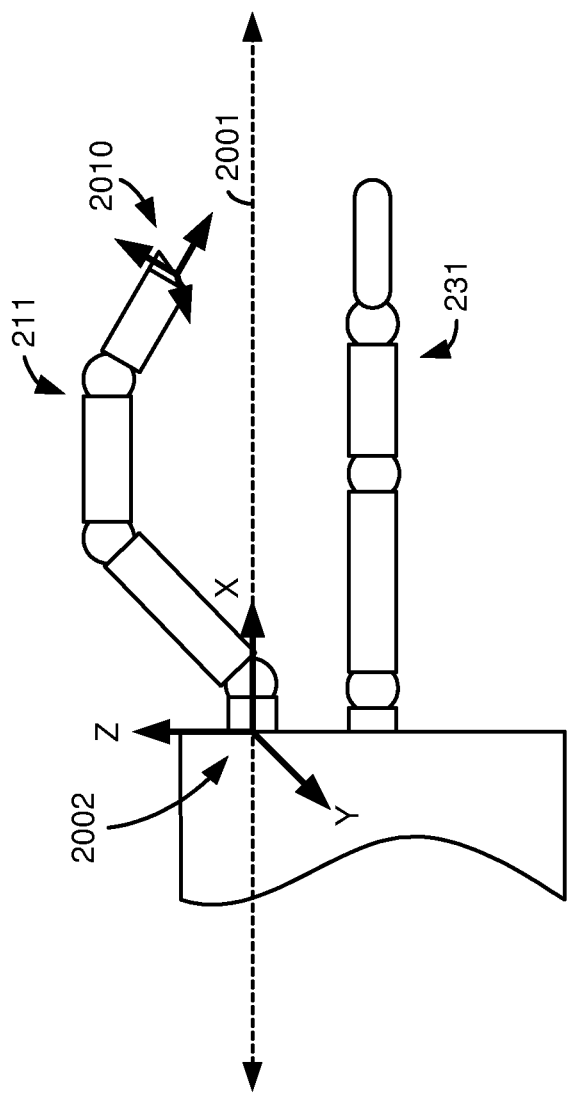
FIG. 20 illustrates a side view of an articulatable camera and articulatable surgical tool extending out of a distal end of an entry guide with a zero position reference frame shown relative to a computer generated auxiliary view as used in a medical robotic system utilizing aspects of the present invention.

As one possible reference frame that may be used, FIG. 20 illustrates a so-called "zero position" reference frame 2002 which corresponds to the position and orientation where the joints 323, 325, 327 are rotated so that the links 321, 324, 326 are in a straight line and their insertion position is a fully retracted position (i.e., the camera tip 311 is just inside the passage 321 of the entry guide 200). In this position, a reference frame defined at the camera tip (i.e., the camera reference frame 2010) coincides with the "zero position" reference frame 2002. This frame has the property of being aligned with the entry guide 200 and is centered with respect to the workspace of the camera tip 311. Therefore, the range of motion limits (perceived by the operator through haptic feedback on the input device 108) can be used to find the center position of the camera tip 311 and the operator can easily understand how the camera instrument 211 moves in response to the motions of his or her arm/hand. In other words, the kinesthetic mapping between user arm/hand and camera tip 311 is aligned to the visual mapping between the camera motion and the auxiliary view seen by the Surgeon at the console 104 and/or auxiliary display 140.

Figure 21:
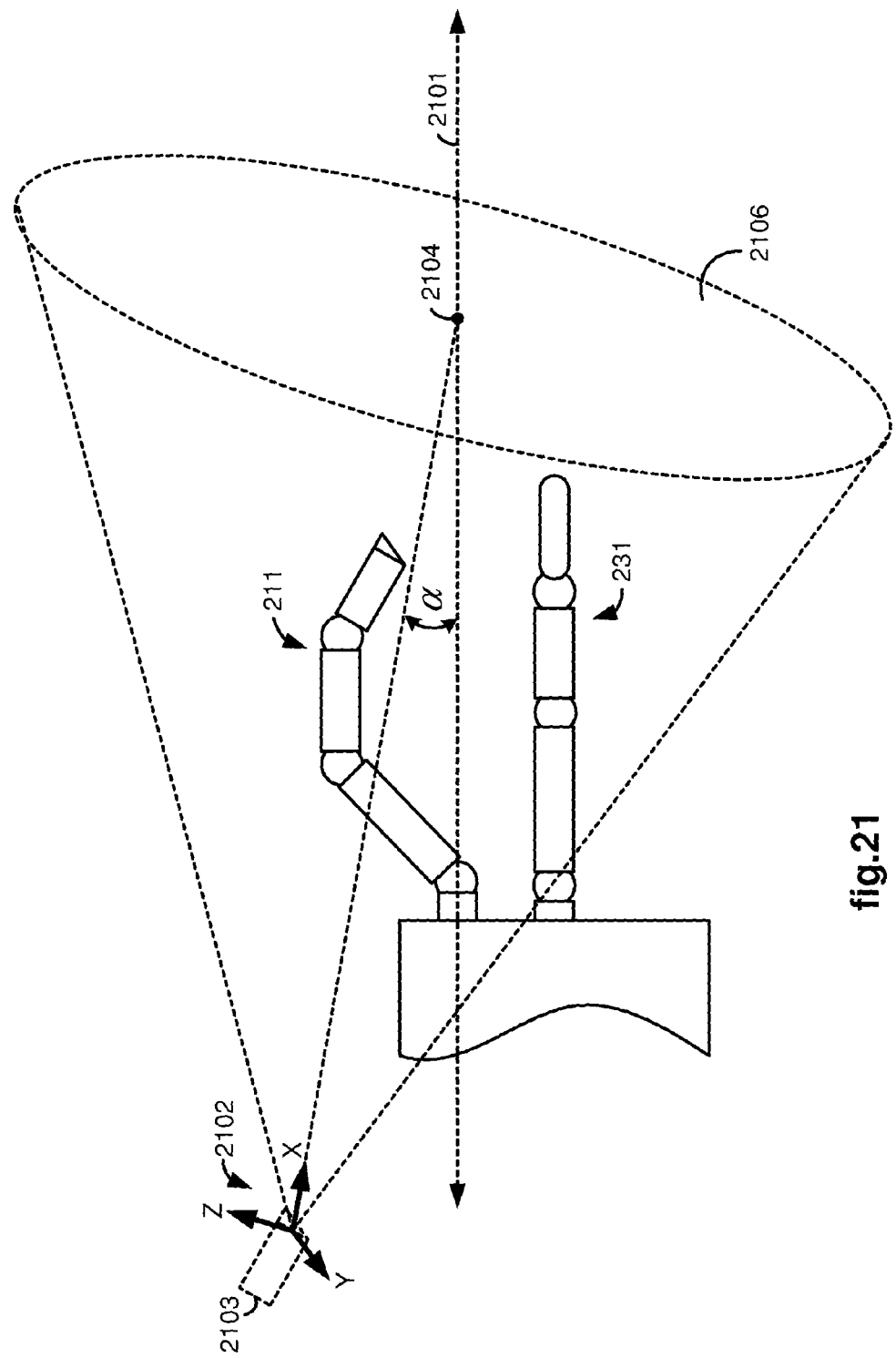
FIG. 21 illustrates a side view of an articulatable camera and articulatable surgical tool extending out of a distal end of an entry guide with an isometric auxiliary view reference frame shown relative to a computer generated auxiliary view as used in a medical robotic system utilizing aspects of the present invention.

As another possible reference frame that may be used, FIG. 21 illustrates an "isometric auxiliary view" reference frame 2102 which corresponds to a viewing point of the auxiliary view being displayed on the auxiliary display 140 (such as shown in FIG. 12) and/or monitor 104 (such as shown in window 1502 of FIG. 15). The viewing point in this case may be thought of as a view taken from the perspective of a virtual camera 2103 whose position and orientation is preferably fixed in space during the camera positioning mode. The reference frame 2102 is defined at the tip (i.e., viewing end) of the virtual camera 2103 and its position and orientation are computed so that it has an azimuth angle $\alpha$ with respect to a focal point 2104 (of the virtual camera 2103) on the central longitudinal axis 2101 of the passage 321 of the entry guide 200 through which the camera instrument 211 extends. In particular, the location of the focal point 2104 along the longitudinal axis 2101 and the size of the azimuth angle $\alpha$ are selected so that the virtual camera 2103 has a slight elevation that provides adequate depth perception in the isometric rendering of the auxiliary view and its field of view 2106 includes the links of the camera instrument 211 and surgical tool 231 during the camera positioning mode. User studies have indicated that an angle α of approximately 25 degrees is particularly desirable for this purpose. The symmetry properties of the "zero position" reference frame are also applicable in the "auxiliary view" reference frame, with the potential advantage that the operator can use the isometric view to drive the position and orientation of the camera tip 311 and have entirely consistent haptic feedback in that frame.

In 1904, the orientation of a hand-grippable part of the input device 108 (referred to herein as the "master orientation") is aligned so that the master orientation with respect to a computer generated auxiliary view of the camera, which is being displayed on the 3-D monitor 104, is the same as the current orientation of the camera tip 311 with respect to the reference frame computed in 1903 for camera control. Alternatively, this orientation alignment may be avoided by, for example, computing and accounting for the offset between the current master orientation and the current camera orientation so that the master angular motions with respect to the initial orientation are used to command the movement of the camera tip 311.

In 1905, the current position of the hand-grippable part of the input device 108 is mapped to the current position of the camera tip 311 so as to cancel translational offsets, and in 1906, user-selectable scaling factors are set between the input device 108 and the camera 211 workspaces.

In 1907, the camera controller (CTRLC) 213 is enabled so that the input device 108 now controls the positioning and orienting of the articulatable camera instrument 211 through the camera controller (CTRLC) 213 and manipulator (ECM) 212, and in 1908, the camera tip 311 is moved to the desired position and/or orientation. A description of the camera controller 213 using the control reference frame is provided below in reference to FIG. 22.

Once the camera tip 311 has been positioned and/or oriented as desired, then the method performs preparatory tasks 1909-1910 before enabling control over the tool 241 by the input device 108 in 1911. In particular, in 1909, the camera 211 is soft-locked so that it is commanded to remain in its present stationary state (i.e., the desired position and/or orientation) by the camera controller 213, and in 1910, the master orientation is aligned with that of the tool 241.

Figure 22:
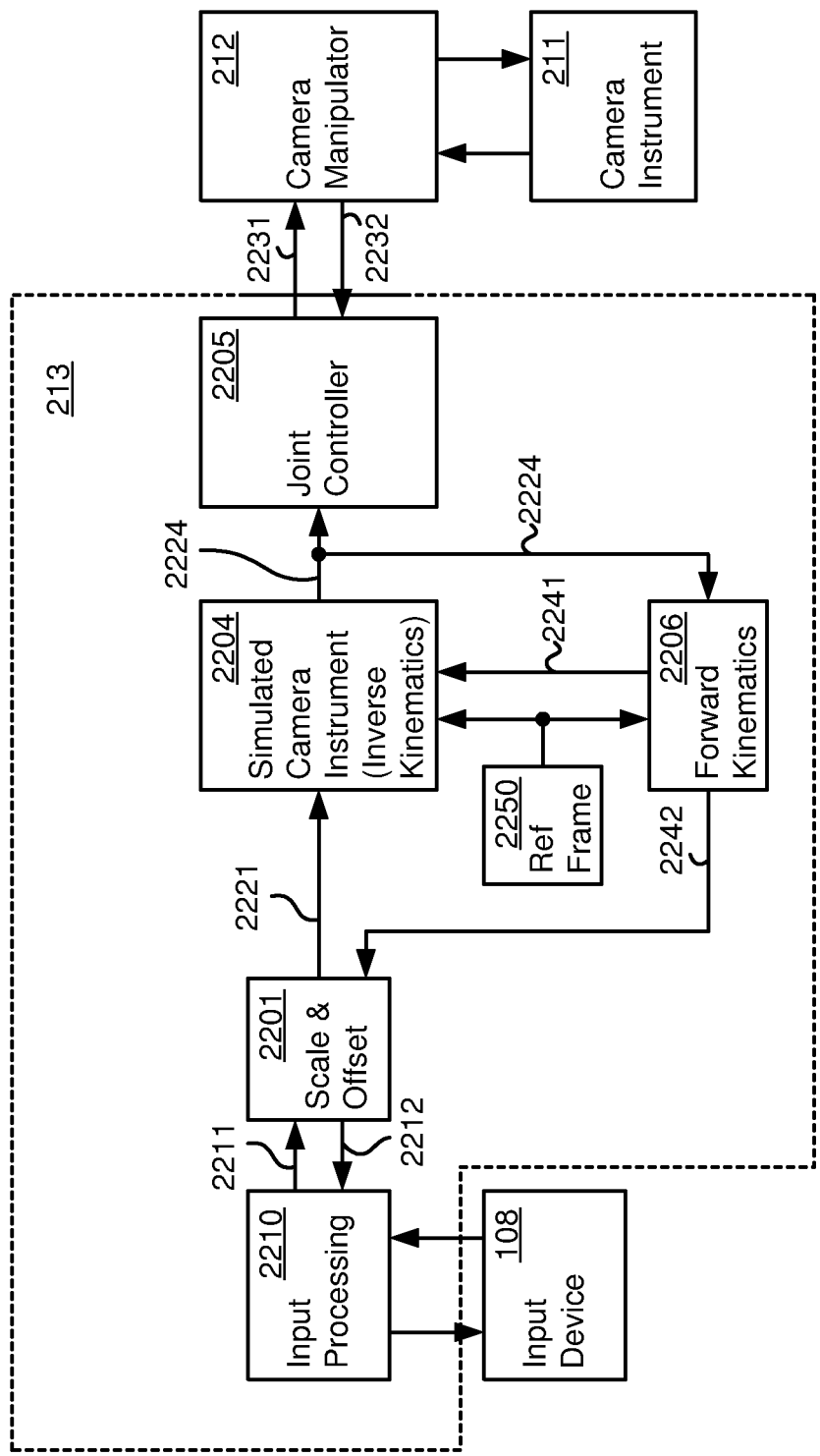
FIG. 22 illustrates a block diagram of a camera controller as used in a medical robotic system utilizing aspects of the present invention.

FIG. 22 illustrates, as an example, a block diagram of the camera controller (CTRLC) 213 for controlling movement of the camera manipulator (ECM) 212 (also referred to herein as "slave manipulator" or "slave") and consequently, the position and orientation of the tip 311 of the camera instrument 211, as commanded by movement of the input device 108 (also referred to herein as "master manipulator" or "master") by the Surgeon.

The input device 108 includes a number of links connected by joints so as to facilitate multiple degrees-of-freedom movement. For example, as the Surgeon moves the input device 108 from one position to another, sensors associated with the joints of the input device 108 sense such movement at sampling intervals (appropriate for the processing speed of the controller 102 and camera control purposes) and provide digital information indicating such sampled movement in joint space to input processing block 2210.

Input processing block 2210 processes the information received from the joint sensors of the input device 108 to transform the information into a corresponding desired position and velocity for the camera tip 311 in its Cartesian space relative to a reference frame associated with the position of the Surgeon's eyes (the "eye reference frame") by computing a joint velocity from the joint position information and performing the transformation using a Jacobian matrix and eye related information using well-known transformation techniques.

Scale and offset processing blocks 2201 receives the processed information 2211 from the input processing block 2210 and applies scale and offset adjustments to the information so that the resulting movement of the camera tip 311 and consequently, its computer generated auxiliary view being viewed by the Surgeon at the time on the monitor 104 and/or auxiliary display 140 appears natural and as expected by the Surgeon. The scale adjustment is useful where small movements of the camera tip 311 are desired relative to larger movement of the input device 108 in order to allow more precise movement of the camera tip 311 as it views the work site. An offset adjustment is applied for aligning the input device 108 with respect to the Surgeon's eyes as he or she manipulates the input device 108 to command movement of the camera tip 311 through the auxiliary view that is being displayed at the time on the monitor 104 and/or auxiliary display 140.

A simulated camera block 2204 receives the output 2221 of the scale and offset processing block 2201 and transforms the commanded position and velocity for the camera tip 311 from the Cartesian space of the eye reference frame to the joint space of the camera manipulator 212 using its inverse kinematics while avoiding singularities in its operation and limiting the commanded joint positions and velocities to avoid physical limitations or other constraints such as avoiding harmful contact with tissue or other parts of the Patient. To perform such transformation, a mapping is performed between the eye frame and the control reference frame (provided by the reference frame computation block 2250) and another mapping is performed between a tip of the hand-grippable part of the master 108 and the camera tip 311. Note that these mappings preserve orientations while offsets are compensated for in the scale and offset block 2201. Once the mappings are established, the inverse and forward kinematics blocks 2204, 2206 use this information to perform their computations since the mappings describe the positions and orientations of the master and camera tips with respect to the control reference frame.

The output 2224 of the simulated camera block 2204 is then provided to a joint controller block 2205 and a forward kinematics block 2206. The joint controller block 2205 includes a joint control system for each controlled joint (or operatively coupled joints such as "joggle joints") of the camera instrument 211 (such as translational and orientational assemblies shown and described in reference to FIG. 8). The output 2224 of the simulated camera block 2204 provides the commanded value for each joint of the camera instrument 211. For feedback control purposes, sensors associated with each of the controlled joints of the camera instrument 211 provide sensor data 2232 back to the joint controller block 2205 indicating the current position and/or velocity of each joint of the camera instrument 211. The sensors may sense this joint information either directly (e.g., from the joint on the camera instrument 211) or indirectly (e.g., from the actuator in the camera manipulator 212 driving the joint). Each joint control system in the joint controller 2205 then generates torque commands for its respective actuator in the camera manipulator 212 so as to drive the difference between the commanded and sensed joint values to zero in a conventional feedback control system manner.

The forward kinematics block 2206 transforms the output 2224 of the simulated camera block 2204 from joint space back to Cartesian space relative to the eye reference frame using the forward kinematics of the camera instrument 211 with respect to the control reference frame (provided by the reference frame computation block 2250). The scale and offset block 2201 performs an inverse scale and offset function on the output 2242 of the forward kinematics block 2206 before passing its output 2212 to the input processing block 2210 where an error value is calculated between its output 2211 and input 2212. If no limitation or other constraint had been imposed on the input 2221 to the simulated camera block 2204, then the calculated error value would be zero. On the other hand, if a limitation or constraint had been imposed, then the error value is not zero and it is converted to a torque command that drives actuators in the input device 108 to provide force feedback felt by the hands of the Surgeon. Thus, the Surgeon becomes aware that a limitation or constraint is being imposed by the force that he or she feels resisting his or her movement of the input device 108 in that direction. In addition to this force feedback, forces coming from other sensors or algorithms (e.g., a force/pressure sensor or an algorithm to avoid the work volume of the surgical tools to prevent collisions) may be superimposed on the force feedback.

An output 2241 of the forward kinematics block may also be provided to the simulated camera block for control purposes. For example, the simulated position output may be fed back and compared with the commanded position.

Although the various aspects of the present invention have been described with respect to a preferred embodiment, it will be understood that the invention is entitled to full protection within the full scope of the appended claims.

We claim:

1. A method for positioning and orienting a distal end of an image capturing device that is controllably movable in response to operator manipulation of an input device by actuating a plurality of joints that is mechanically coupled to a plurality of links which is mechanically coupled to the distal end of the image capturing device, the method comprising:
   receiving information of positions of the plurality of joints;
   determining a position and orientation of the distal end of the image capturing-device by using the received information of the positions of the plurality of joints;
   generating a virtual camera perspective view of a computer model of the distal end of the image capturing device, of at least one of the plurality of links, and of at least one of the plurality of joints by using the determined position and orientation of the distal end of the image capturing device, wherein the virtual camera perspective view is from a perspective of a virtual camera;
   displaying the virtual camera perspective view of the computer model on a display screen; and
   controlling the positioning and orienting of the distal end of the image capturing device by actuating the plurality of joints in response to operator manipulation of the input device such that movement of the input device results in corresponding scaled movement of the distal end of the image capturing device relative to a control reference frame so that the positioning and orienting of the distal end of the image capturing device appears to an operator who is manipulating the input device while viewing the display screen to be intuitively correct with respect to the displayed virtual camera perspective view of the computer model.

2. The method according to claim 1, wherein the plurality of joints is included in a manipulator used for positioning and orienting the distal end of the image capturing device;
   wherein the receiving information of the positions of the plurality of joints comprises: receiving information from a sensor disposed in proximity to the distal end of the image capturing device; and
   wherein the determining the position and orientation of the distal end of the image capture device comprises: calculating calculated positions of the plurality of joints by applying the information received from the sensor to inverse kinematics of the manipulator, and calculating the position and orientation of the distal end of the image capture device by applying the calculated positions of the plurality of joints to forward kinematics of the manipulator.

3. The method according to claim 1, wherein the plurality of joints is included in a manipulator used for positioning and orienting the distal end of the image capturing device;
   wherein the determining the position and orientation of the distal end of the image capture device comprises: calculating the position and orientation of the distal end of the image capturing device by applying the received information of the positions of the plurality of joints to forward kinematics of the manipulator.

4. The method according to claim 1, wherein the generating of the virtual camera perspective view of the computer model comprises:
   generating a three-dimensional computer model of the distal end of the image capturing device, the plurality of joints, and the plurality of links; and
   translating and orienting the generated three-dimensional computer model to the virtual camera perspective view.

5. The method according to claim 1, wherein the distal end of the image capture device and at least one articulatable instrument extends out of an entry guide, and the virtual camera perspective view is at a position and orientation from which a distal end of the at least one articulatable instrument, the distal end of the image capturing device, the at least one of the plurality of links, and the at least one of the plurality of joints are within the field of view of the virtual camera.

6. The method according to claim 5, wherein the controlling the positioning and orienting of the distal end of the image capturing device-comprises:
   defining the control reference frame such that an origin of the control reference frame is at the position of the virtual camera and such that one axis of the control reference frame points toward a point on a longitudinal axis extending through proximal and distal ends of the entry guide.

7. The method according to claim 5, wherein the controlling the positioning and orienting of the distal end of the image capturing device comprises:
   defining the control reference frame such that an origin of the control reference frame is at a point where the distal end of the image capturing device extends out of the entry guide and such that one axis of the control reference frame is parallel with a central longitudinal axis of the entry guide.

8. A medical system comprising:
   an image capturing device having a distal end;
   a plurality of links that is mechanically coupled to the distal end of the image capturing device for positioning and orienting the distal end of the image capturing device;
   a plurality of joints that is mechanically coupled to the plurality of links;
   a display screen;
   an input device; and
   a controller configured: to receive information of positions of the plurality of joints; to determine a position and orientation of the distal end of the image capturing device by using the received information of the positions of the plurality of joints; to generate a virtual camera perspective view of a computer model of the distal end of the image capturing device, of at least one of the plurality of links, and of at least one of the plurality of joints by using the determined position and orientation of the distal end of the image capturing device, wherein the virtual camera perspective view is from a perspective of a virtual camera; to display the virtual camera perspective view of the computer model on the display screen; and to control the positioning and orienting of the distal end of the image capturing device by actuating the plurality of joints in response to manipulation of the input device such that movement of the input device results in corresponding scaled movement of the distal end of the image capturing device relative to a control reference frame so that the positioning and orienting of the distal end of the image capturing device appears to an operator who is manipulating the input device while viewing the display screen to be intuitively correct with respect to the displayed virtual camera perspective view of the computer model.

9. The medical system according claim 8, wherein the controller is configured to determine the positions of the plurality of joints by using information provided by sensors that sense the positions of the plurality of joints.

10. The medical system according claim 8, further comprising: actuators used to actuate the plurality of joints, wherein the controller is configured to determine the positions of the plurality of joints by using information provided by encoders that sense actuation of the actuators.

11. The medical system according claim 8, wherein the plurality of joints is included in a manipulator used for positioning and orienting the distal end of the image capturing device, and the controller is configured to determine the positions of the joints by receiving information from a sensor disposed in proximity to the distal end of the image capturing device and by calculating the positions of the plurality of joints by applying the information received from the sensor to inverse kinematics of the manipulator.

12. The medical system according claim 8, wherein the plurality of joints is included in a manipulator used for positioning and orienting the distal end of the image capturing device, and the controller is configured to calculate the position and orientation of the distal end of the image capturing device by applying the received information of the positions of the plurality of joints to forward kinematics of the manipulator.

13. The medical system according claim 8, wherein the controller is configured to generate the virtual camera perspective view of the computer model by generating a three-dimensional computer model of the distal end of the image capturing device, the plurality of joints, and the plurality of links; and by translating and orienting the three-dimensional computer model to the virtual camera perspective.

14. The medical system according to claim 8, further comprising: at least one articulatable instrument, wherein the distal end of the image capturing device and a distal end of the at least one articulatable instrument extends out of an entry guide, and the virtual camera perspective view is at a position and orientation from which the distal end of the at least one articulatable instrument, the distal end of the image capturing device, the at least one of the plurality of links, and the at least one of the plurality of joints are within the field of view of the virtual camera.

15. The medical system according to claim 14, wherein the control reference frame has an origin at the position of the virtual camera and is oriented such that one axis of the control reference frame points to a point on a longitudinal axis extending through proximal and distal ends of the entry guide.

16. The medical system according to claim 14, wherein the control reference frame has an origin where the distal end of the image capturing device extends out of the entry guide and is oriented such that one axis of the control reference frame is parallel with a central longitudinal axis of the entry guide.

* * * * *